US 8,226,941 B2

Jul. 24, 2012

(12) United States Patent
Caggiano et al.

(10) Patent No.: US 8,226,941 B2
(45) Date of Patent: Jul. 24, 2012

(54) METHODS OF PURIFYING CHONDROITINASE AND STABLE FORMULATIONS THEREOF

(75) Inventors: Anthony O. Caggiano, Larchmont, NY (US); Elliott A. Gruskin, Killington, CT (US); Yelena G. Sheptovitsky, Stamford, CT (US); Sarah Kasperbauer, Cortlandt Manor, NY (US)

(73) Assignee: Acorda Therapeutics, Inc., Hawthorne, NY (US)

( * ) Notice: Subject to any disclaimer, the term of this patent is extended or adjusted under 35 U.S.C. 154(b) by 951 days.

(21) Appl. No.: 11/568,831

(22) PCT Filed: May 18, 2005

(86) PCT No.: PCT/US2005/017464
§ 371 (c)(1),
(2), (4) Date: Aug. 22, 2008

(87) PCT Pub. No.: WO2005/112986
PCT Pub. Date: Dec. 1, 2005

(65) Prior Publication Data
US 2008/0311642 A1 Dec. 18, 2008

Related U.S. Application Data

(60) Provisional application No. 60/572,030, filed on May 18, 2004, provisional application No. 60/621,882, filed on Oct. 25, 2004.

(51) Int. Cl.
*A61K 38/46* (2006.01)
*A61K 38/47* (2006.01)
*C12N 9/24* (2006.01)
*C07H 21/04* (2006.01)

(52) U.S. Cl. .......... 424/94.62; 424/94.6; 424/94.61; 435/200; 536/23.2

(58) Field of Classification Search .......... None
See application file for complete search history.

(56) References Cited

U.S. PATENT DOCUMENTS

| | | | |
|---|---|---|---|
| 5,262,522 A | 11/1993 | Gearing | |
| 5,270,194 A * | 12/1993 | D'Alterio et al. ........ | 435/188 |
| 5,496,718 A | 3/1996 | Hashimoto | |
| 5,498,536 A | 3/1996 | Khandke | |
| 5,578,480 A | 11/1996 | Khandke | |
| 5,652,122 A | 7/1997 | Frankel et al. | |
| 5,670,617 A | 9/1997 | Frankel et al. | |
| 5,674,980 A | 10/1997 | Frankel et al. | |
| 5,747,641 A | 5/1998 | Frankel et al. | |
| 5,763,205 A | 6/1998 | Hashimoto et al. | |
| 5,792,743 A | 8/1998 | Schachner | |
| 5,804,604 A | 9/1998 | Frankel et al. | |
| 5,869,301 A | 2/1999 | Nghiem et al. | |
| 5,997,863 A | 12/1999 | Zimmermann et al. | |
| 6,007,810 A | 12/1999 | Ishikawa | |
| 6,063,378 A | 5/2000 | Nohara et al. | |
| 6,093,563 A | 7/2000 | Bennett et al. | |
| 6,153,187 A | 11/2000 | Yacoby-Zeevi | |
| 6,171,575 B1 | 1/2001 | Okuyama | |
| 6,184,023 B1 * | 2/2001 | Hashimoto et al. ........ | 435/232 |
| 6,200,564 B1 | 3/2001 | Lamont et al. | |
| 6,248,562 B1 | 6/2001 | Dunn et al. | |
| 6,313,265 B1 | 11/2001 | Phillips et al. | |
| 6,326,166 B1 | 12/2001 | Pomerantz et al. | |
| 6,972,168 B2 | 12/2005 | Muir et al. | |
| 7,008,783 B1 | 3/2006 | Sato et al. | |
| 7,074,581 B2 | 7/2006 | Yamashita et al. | |
| 7,163,545 B2 | 1/2007 | Yaszemski et al. | |
| 7,465,705 B2 | 12/2008 | Lee et al. | |
| 7,507,570 B2 * | 3/2009 | Prabhakar et al. ........ | 435/232 |
| 7,560,106 B2 * | 7/2009 | Sasisekharan et al. ...... | 424/94.5 |
| 2003/0040112 A1 | 2/2003 | Muir et al. | |
| 2003/0072749 A1 | 4/2003 | Muir et al. | |
| 2003/0077258 A1 | 4/2003 | Muir | |
| 2004/0033221 A1 | 2/2004 | Masuda et al. | |
| 2004/0265297 A1 | 12/2004 | Gruskin et al. | |
| 2005/0118157 A1 | 6/2005 | McMahon et al. | |
| 2005/0233419 A1 | 10/2005 | Pojasek et al. | |
| 2006/0078959 A1 | 4/2006 | Prabhakar et al. | |
| 2006/0153827 A1 | 7/2006 | Gruskin et al. | |
| 2006/0233782 A1 | 10/2006 | Gruskin et al. | |
| 2007/0104703 A1 | 5/2007 | Caggiano et al. | |
| 2007/0274979 A1 | 11/2007 | Gruskin et al. | |

FOREIGN PATENT DOCUMENTS

| | | |
|---|---|---|
| AU | 2003/208466 B2 | 9/2003 |
| AU | 2004241088 A2 | 12/2004 |
| EP | 0704532 A2 | 3/1996 |
| EP | 1646353 A2 | 4/2006 |
| JP | H06-153947 | 6/1994 |
| JP | H10-174598 | 6/1998 |
| JP | H1-500308 | 1/1999 |
| JP | H11-236336 | 8/1999 |

(Continued)

OTHER PUBLICATIONS

Sato et al., Cloning and Expression in *Escherichia coli* of the Gene Encoding the *Proteus vulgaris* Chondroitin ABC Lyase, Jan. 1, 1994, Appl. Microbiol. Biotechnol., 41:39-46.
Accession P59807, Aug. 15, 2003 *UniProtKB/Swiss-Prot*.
Aldrich "Enzymer Explorer" 2009, URL:http://vvww.sigmaaldrich.com/life-science/metabolomics/enzyme-explorer/learning-center/carbohydrate-analysis/carbohydrate-analysis-iii.
Anderson et al. "Tumor Cell Retention of Antibody Fab Fragments is Enhanced by an Attached HIV TAT Protein-Derived Peptide" 1993, *Biochem. & Biophys. Res. Commun.* 194(2):876-884.

(Continued)

*Primary Examiner* — Anand Desai
*Assistant Examiner* — Iqbal H Chowdhury
(74) *Attorney, Agent, or Firm* — Pepper Hamilton LLP

(57) ABSTRACT

An aspect of the present invention relates to stable formulations of chondroitinase and to methods of purifying chondroitinase. The methods of purifying chondroitinase includes the steps of extracting the enzyme from a cell, separating the chondroitinase from the crude cell extract using cation-exchange chromatography, removing impurities through gel filtration chromatography, and removing endotoxin through an anion-exchange membrane to produce a purified chondroitinase.

17 Claims, 15 Drawing Sheets

FOREIGN PATENT DOCUMENTS

| | | |
|---|---|---|
| JP | 2002/505873 | 2/2002 |
| JP | 2002/526028 | 8/2002 |
| JP | 2003/500016 | 1/2003 |
| JP | 2004-89191 | 3/2004 |
| JP | 2004-113166 | 4/2004 |
| WO | WO 91/06303 A | 5/1991 |
| WO | WO 94/25567 A1 | 11/1994 |
| WO | WO 95/13091 A1 | 5/1995 |
| WO | WO 99/40787 A1 | 8/1999 |
| WO | WO 99/46368 A2 | 9/1999 |
| WO | WO 00/52149 A1 | 9/2000 |
| WO | WO 00/62067 A1 | 10/2000 |
| WO | WO 00/64482 A1 | 11/2000 |
| WO | WO 00/75319 A1 | 12/2000 |
| WO | WO 01/39795 A2 | 6/2001 |
| WO | WO 02/08285 A2 | 1/2002 |
| WO | WO 02/055684 A | 7/2002 |
| WO | WO 02/065136 A2 | 8/2002 |
| WO | WO 02/083179 A2 | 10/2002 |
| WO | WO 03/000901 A2 | 1/2003 |
| WO | WO 03/015612 A2 | 2/2003 |
| WO | WO 03/022882 A2 | 3/2003 |
| WO | WO 03/031578 A2 | 4/2003 |
| WO | WO 03/074080 A1 | 9/2003 |
| WO | WO 03/100031 A2 | 12/2003 |
| WO | WO 03/102160 A2 | 12/2003 |
| WO | WO 2004/017044 A2 | 2/2004 |
| WO | WO 2004/103299 A2 | 12/2004 |
| WO | WO 2004/110359 A2 | 12/2004 |
| WO | WO 2004/110360 A2 | 12/2004 |
| WO | WO 2005/087920 A2 | 9/2005 |
| WO | WO 2007/038548 A2 | 4/2007 |

OTHER PUBLICATIONS

Appel et al. "Several Extracellular Domains of the Neural Cell Adhesion Molecule L1 are Involved in Neurite Outgrowth and Cell Body Adhesion" 1993, *J. Neurosc.* 13(11): 4764-4775.

Avrameas et al. "Polyreactive anti-DNA monoclonal antibodies and a derived peptide as vectors for the intracytoplasmic and intranuclear translocation of macromolecules" 1998, *Proc. Natl. Acad. Sci. USA* 95:5601-5606.

Banker et al. "Modern Pharmaceutics" 1979, *Marcel Dekker, Inc.* (TOC).

Banker et al. "Modern Pharmaceutics" 4th Ed., 2002, *Informa Healthcare*, New York (TOC).

Bao et al. "A Functional Dermatan Sulfate Epitope Containing Iduronate (2-O-sulfate) α1-3GalNAC (6-O-sulfate) Disaccharide in the Mouse Brain" 2005, *J. of Bio. Chem.* 280(24):23184-23193.

Basso et al. "A Sensitive and Reliable Locomotor Rating Scale for Open Field Testing in Rats" 1995, *J. of Neurotrama* 12(1):1-21.

Bixby et al. "Neurite outgrowth on muscle cell surfaces involves extracellular matrix receptors as well as Ca2+-dependent and -independent cell adhesion molecules" 1987, *Proc. Natl. Acad. Sci. USA* 84:2555-2559.

Bowie et al. "Deciphering the Message in Protein Sequences: Tolerance to Amino Acid Substitutions" 1990, *Science* 247:1306-1319.

Bradbury et al. "Chondroitinase ABC Promotes Regeneration and Functional Recovery Following Spinal Cord Injury" 2001, *Soc. for Neuroscience Abstracts* 27(2):1835.

Bradbury et al. "NT-3 Promotes Growth of Lesioned Adult Rat Sens Ory Axons Ascending in the Dorsal Columns of the Spinal Cord" 1999, *Eur. J. Neurosc.* 11(11):3873-3783.

Bray et al., Neuronal and Nonneuronal Influences on Retinal Ganglion Cell Survival, Axonal Regrowth, and Connectivity after Axotomy, 1991, *Ann. NY Acad. Sci.*, 214-228.

Burgess et al. "Possible Dissassociation of the Heparin-binding and Mitogenic Activities of Heparin-binding (Acidic Fibroblast) Growth Factor-1 From Its Receptor-binding Activities by Site-directed Mutagenesis of a Single Lysine Residue" 1990, *J. of Cell. Bio.* 111:2129-2138.

Cadelli et al. "Oligodendrocyte- and Myelin-Associated Inhibitors of Neurite Outgrowth: Their Involvement in the Lack of CNS Regeneration" 1992, *Exp. Neur.* 115:189-192.

Caggiano et al. "Chondroitinase ABCI Improves Locomotion and Bladder Function following Contusion Injury of the Rat Spinal Cord" 2005, *J. Neurotrauma* 22(2):226-239.

Cajal "Degeneration & Regeneration of the Nervous System" May ed., 1959, *Hafner Publ. Co.*, New York (TOC).

Chang et al. "Extension of Neurites on Axons is Impaired by Antibodies against Specific Neural Cell Surface Glycoproteins" 1987, *J. Cell. Biol.* 104:355362.

Chen et al. "Peripheral nerve regeneration using silicone rubber chambers filled with collagen, laminin and fibronectin" 2000, *Biomat.* 21:1541-1547.

Degrendele et al. "Requirement for CD44 in Activated T Cell Extravassation into an Inflammatory Site" 1997, *Science* 78:672-675.

Denuziere et al. "Chitosan-Chondroitin sulfate and chitosan-hyaluronate polyelectrolyte complexes: biological properties" 1998, *Biomaterials* 19:1275-1285.

Derossi et al. "Cell Internalization of the Third Helix of the Antennapedia Homeodomain is Receptorindependent" 1996, *J. Biol. Chem* 271:18188-18193.

Doppenberg et al. "Clinical Trials in Traumatic Brain Injury" 1998, *Ann. NY Acad. Sci.* 305-319.

Edelman "Cell Adhesion Molecules" 1983, *Science* 219:450-457.

Edelman et al. "Morphoregulatory Molecules" 1990, *Wiley, New York* (TOC).

Efthymiadis et al. "The HIV-1 Tat Nuclear Localization Sequence Confers Novel Nuclear Import Properties" Jan. 16, 1998, *J. Biol. Chem.* 273(3):1623-1628.

Ellioit et al. "Intercellular Trafficking and Protein Delivery by a Herpesvirus Structural Protein" 1997, *Cell* 88:223-233.

Fahraeus et al. "Inhibition of pRb phosphorylation and cell-cycle progression by a 20-residue peptide derived from p16CDKN2IINK4A" 1996, *Curr. Biol.* 6(1):84-91.

Favre et al. "Hyaluronidase enhances recombinant adeno-associated virus (rAAV)-mediated gene transfer in the rat skeletal muscle" 2000, *Gene Ther.* 7(16):1417-1420.

Fawell et al. "Tat-mediated delivery of heterologous proteins into cells" 1994, *Proc. Natl. Acad. Sci. USA* 91:664-668.

Fethiere et al. "Crystal Structure of Chondroitin AC Lyase, a Representative of a family of Glycosaminoglycan Degrading Enzymes" 1999, *J. Mol. Biol.* 288:635-647.

Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.

Frankel et al. "Tat Protein from Human Immunodeficiency Virus Forms a Metal-Linked Dimer" 1988, *Science* 240:70-73.

Frankish et al. "Spinal-cord Repair Moves a Step Closer" 2002, *The Lancet* 359(9314):1317.

Gennaro "Remington's Pharmaceutical Sciences" 1985, *Mack Publishing Company* (PA) 17th Ed. (TOC).

Goodman et al. "The Pharmacological Basis of Therapeutics" 10th ed., 2001, *McGraw Hill*, New York (TOC).

Goodman et al. "The Pharmacological Basis of Therapeutics" 6th ed. 1980, *MacMillan Pub.*, New York (TOC).

Hiyama et al. "Crystallization and Some Properties of Chondroitinase from *Arthrobacter aurescens*" 1975, *J. Biol. Chem.* 250:1824-1828.

Hlavin et al. "Molecular Structure and Functional Testing of Human L1CAM: An Interspecies Comparison" 1991, *Genomics* 11:416-423.

Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.

Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.

Huang et al. "Crystal Structure of Chondroitinase B from *Flavobacterium heparinum* and its Complex with a Disaccharide Product at 107 A Resolution" 1999, *J. Mol. Biol.* 294:1257-1269.

Huang et al. "Crystal Structure of Proteus vulgaris Chondroitin Sulfate ABC Lyase I at 1.9 A Resolution" 2003, *J. Mol. Biol.* 328:623-634.

Iida et al. "Cell Surface Chondroitin Sulfate Proteoglycans in Tumor Cell Adhesion, Motility and Invastion" 1996, *Seminars in Cancer Biology* 7:155-162.

Iwai et al. "Axon Patterning Requires DN-cadherin, a Novel Neuronal Adhesion Receptor, in the Drosphila Embryonic CNS" 1997, *Neuron* 19:77-89.

Jones "Taking a new TAK on Tat transactivation" 1997, *Genes & Dev.* 11:2593-2599.

Jung et al. "Transit time of leutocytes rolling through venules controls cytokine-induced inflammatory cell recruitment in vivo" 1998, *J. Clin. Invest.* 102(8):1526-1533.

Kadmon et al. "Functional Cooperation between the Neural Adhesion Molecules L1 and N-CAM is Carbohydrate Dependent" 1990, *J. Cell Biol.* 110:209-218.

Kadmon et al. "The Neural Cell Adhesion Molecule N-CAM Enhances L1-dependent Cell-Cell Interactions" 1990, *J. Cell Biol.* 110:193-208.

Khan et al. "Animal Models of Spinal Cord Contusion Injuries", 1999, *Laboratory Animal Science* 49(2): 161-172.

Kim et al. "Insertion and Deletion Mutants of FokI Restriction Endonuclease" 1994, *J. Biol. Chem.* 269(50):31978-31982.

Kubota et al. "Functional Similarity of HIV-1 Rev and HTLV-1 Rex Proteins: Identification of a New Nucleolar-Targeting Signal in Rev Protein" Aug. 15, 1989, *Biochem. Biophys. Res. Commun.* 162(3):963-970.

Lagenaur et al. "An L1-like molecule, the 8D9 antigen, is a potent substrate for neurite extension" 1987, *Proc. Natl. Acad. Sci. USA* 84:7753-7757.

Lemons et al. "Chondroitin Sulfate Preteoglycan Immunoreactivity Increases Following Spinal Cord Injury and Transplantation" 1999, *Exper. Neurology* 160:51-65.

Lesley et al. "Variant Cell Lines Selected for Alterations in the Function of the Hyaluronan Receptor CD44 Show Differences in Glycosylation" 1995, *J. Exp. Med.* 182:431-437.

Li et al. "Delayed systemic Nogo-66 Receptor Antagonist Promotes Recovery from Spinal Cord Injury" 2003, *J. Neuroscience* 23(10):4219-4227.

Lindner et al. "L1 mono- and polyclonal antibodies modify cell migration in early postnatal mouse cerebellum" 1983, *Nature* 305:427-430.

Lodish et al. "Integrating cells into tissue" 2000, *Mol. Cell Biology*, 5th Ed., Chapter 6.

Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.

Maniatis et al. "Molecular Cloning: A Laboratory Manual" 1982, *Cold Spring Harbor Lab.* (TOC).

Mann et al. "Endocytosis and Targeting of Exogenous HIV-1 Tat Protein" Jul. 10, 1991, *EMBO J.* 10(7):1733-1739.

Martini et al. "Restricted Localization of L1 and N-CAM Sites of Contact Between Schwann Cells and Neurites in Culture" 1994, *GLIA* 10:70-74.

Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.

Matteuci et al. "Synthesis of Deoxyoligonucleotides on a Polymer Support" 1981, *J. Am. Chem. Soc.* 103:3185-3191.

McGee et al. "The Nogo-66 Receptor:Focusing Myelin Inhibition of Axon Regeneration" 2003, *Trends in Neuroscience* 26(4):193-198.

Michelacci et al. "Isolation and Partial Characterization of an Induced Chondroitinase β from *Flavobacterium heparium*" 1974, *Biochem. & Biophys. Res. Comm.* 56(4):973-980.

Michelacci et al., A Comparative Study Between a Chondroitinase B and a Chondroitinase AC from *Flavobacterium heparinum*, 1975, *Biochem. J.* 151:121-129.

Miura et al. "Analysis of Glycosaminoglycan-Degrading Enzymes by Substrate Gel Electrophoresis (Zymography)" 1995, *Anal. Biochem.* 225:333-340.

Modena et al. "Hylauronidase-injectable microparticles intended for the treatment of extravasation" 1998, *J. Microencapsulation* 15(1):85-92.

Moon et al. "Regeneration of CNS axons back to their target following treatment of adult rat brain with chondroitinase ABC" 2001, *Nature Neurosc.* 4(5): 465-466.

Moos et al. "Neural adhesion molecule L1 as a member of the immunoglobulin superfamily with binding domains similar to fibronectin" 1988, *Nature* 334:701-703.

Nagahara et al. "Transduction of fUll-length TAT fusion proteins into mammalian cells: TAT_p27KIp1 induces cell migration" 1998, *Nat. Med.* 4(12):1449-1452.

Netti et al. "Role of Extracellular Matrix Assembly in Interstitial Transport in Solid Tumors" 2000, *Cancer Res.* 60(9):2497-2503.

Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.

Oermann et al. "The Use of Anti-inflammatory Medications in Cystic Fibrosis" 1999, *Chest* 115:1053-1058.

Olmarker et al. "Chondroitinase ABC (Pharmaceutical Grade) for Chemonucleolysis" 1996, *Spine* 21(17):1952-1956.

Pawson et al. "Assembly of Cell Regulatory systems Through Protein Interaction Domains" 2003, *Science* 300:445-452.

Pillwein et al. "Hyaluronidase Additional to Standard Chemotherapy Improves Outcome for Children with Malignant Tumors" 1998, *Cancer Letters* 131:101-108.

Pojasek et al. "Biochemical Characterization of the Chondroitinase B Active Site" Aug. 23, 2002, *J. Biol. Chem.* 277(34):31179-31186.

Pojasek et al. "Recombinant Expression, Purification, and Kinetic Characterization of Chondroitinase AC and Chondroitinase B from *Flavobacterium heparinum*" 2001, *Biochem, Biophys. Res. Commun.* 286:343-351.

Prabhakar et al. "Biochemical Characterization of the Chondroitinase ABC I Active Site" Aug. 23, 2005, *Biochem. J.* pp. 395-405.

Priestley et al. "Stimulating regeneration in the damaged spinal cord" 2002, *J. Phyl.* 96:123-133.

Rathjen et al. "Immunocytological and biochemical characterization of a new neuronal cell surface component (L1 antigen) which is involved in cell adhesion" 1984, *EMBO J.* 3(1):1-10.

Ratjen et al. "Cystic Fibrosis" 2003, *The Lancet* 361(9358):681-689.

Reich et al. "Small interfering RNA (siRNA) targeting VEGF effectively inhibits ocular neovascularization in a mouse model" 2003, *Molecular Vision* 9:210-216.

Reid et al. "Variants of Human L1 Cell Adhesion Molecule Arise through Alternate Splicing of RNA" 1992, *J. Mol. Neurosc.* 3:127-135.

Roy et al. "Generation of Substantially Smaller Deletion Mutants of Chondroitinase AC and B Those are Biologically Active" Nov. 8-12, 2003, Society for Neuroscience Abstract Viewer and Itinerary Planner, 33rd Annual Meeting of the Society of Neuroscience, New Orleans, LA, *Database Biosis*. (Abstract).

Saito et al. "Enzymatic Methods for the Determination of Small Quantities of Isomeric Chondroitin Sulfates" 1968, *J. Biol. Chem.* 243(7):1536-1542.

Sato et al. "Cloning and expression in *Escherichia coli* of the gene encoding the *Proteus vulgaris* chondroitin ABC-lyase" 1994, *Appl. Microbiol. Biotechnol.* 41:39-46.

Sato, et al. "Subunit Structure of Chondroitinase ABC from *Proteus vulgaris*" 1986 *Agric. Biol. Chem.* 50(4):1057-1059.

Schachner "Functional implications of glial cell recognition molecules" 1990, *Neurosc.* 2:497-507.

Schwab "Nerve fibre regeneration after traumatic lesions of the CNS; progress and problems" 1991, *Phil. Trans. R. Soc. Lond.* 331:303-306.

Schwarze et al. "In Vivo Protein Transduction: Delivery of a Biologically Active Protein into the Mouse" 1999, *Science* 285:1569-1572.

Seikagaku Biobus. Corp. "Chondroitinase AC II pamphlet" 2009, URL:http/www.seikagakubb.co.jp/bio/cgi-bin/search/tenpu_pdf/100335.pdf.

Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Bio.* 107:341-351.

Silver et al. "Postnatally induced formation of the corpus callosum in acallosal mice on glia-coated cellulose bridges" 1983, *Science* 220:1067-1069.

Smith-Thomas et al. "Increased Axon Regeneration in Astrocytes Grown in the Presence of Proteoglycan Synthesis Inhibitors" 1995, *J. of Cell Science* 108(3):1307-1315.

Southern "Detection of Specific Sequences Among DNA Fragments Separated by Gel Electrophoresis" 1975, *J. Mol. Biol.* 98:503-517.

Stedman's Medical Dictionary 2000, Lippincott Williams & Wilkins, 27th Ed.

Sterne et al. "Neurotrophin-3 Delivered Locally via Fibronectin Mats Enhances Peripheral Nerve Regeneration" 1997, *Eur. J. Neurosc.* 9:1388-1396.

Tona et al. "Effect of Hyaluronidase on Brain Extracellular Matrix in Vivo and Optic Nerve Regeneration" 1993, *J. Neurosc. Res.* 36:191-199.

Trigg et al. "Peripheral Nerve Regeneration: Comparison of Laminin and Acidic Fibroblast Growth Factor" 1998, *Am. J. Otolaryngology* 19(1):29-32.

Tsuda et al. "Substrate Specificity Studies of *Flavobacterium* Chondroitinase C and Heparitinases Towards the Glycosaminoglycan-protein Linkage region" 1999, *European J. of Biochem.* 262:127-133.

Vives et al. "A Truncated HIV-1 Tat Protein Basic Domain Rapidly Translocates through the Plasma Membrane and Accumulates in the Cell Nucleus" 1997, *J. Biol. Chern.* 272(25):16010-16017.

Vives et al. "Effects of the Tat Basic Domain on Human Immunidefieciency Virus Type 1 Transactivation, Using Chemically Synthesized Tat Protein and Tat Peptides" May 1994, *J. Virol.* 68(5):3343-3353.

Williams et al. "Calcium Influx into Neurons Can Solely Account for Cell Contact-dependent Neurite Outgrowth Stimulated by Transfected L1" 1992, *J. Cell Biol.* 119(4):883-892.

Wood et al. "Inhibition of Schwann Cell Myelination in vitro by Antibody to the L1 Adhesion Molecule" 1990, *J. Neurosc.* 10(11):3635-3645.

Yamagata et al. "Repression of a Malignant Cell-Substratum Adhesion Phenotype by Inhibiting the Production of the Anti-Adhesive Proteoglycan, PG-MNersican" 1994, *J. of Cell Science* 1007:2581-2590.

Yang et al. "Developmental Regulation of a Matrix Metalloproteinase during Regeneration of Axolotl Appendages" 1994, *Dev. Biol.* 166:696-703.

Yang et al. "Expression of Mmp-9 and Related Matrix Metalloproteinase Genes During Axolotl Limb Regeneration" 1999, *Dev. Dyn.* 216:2-9.

Yasuda et al. "Effect of Hyluronidase on Experimental Cerebral Infarct Size and Mortality" 1982, *Lab. Invest.* 46:400-404.

Yick et al. "Chondroitinase ABC promotes axonal regeneration of Clarke's neurons after spinal cord injury" 2000, *Regeneration and Transpl.* 11(5):1063-1067.

Yick et al. "Chondroitinase ABC Promotes Axonal Regrowth of Clarke's Neurons Into Peripheral Nerve Graft After Hemisection of the Spinal Cord" 1999, *Soc. for Neuroscience Abstracts* 25:747.

Matinysn, L.A., Restoration of Functions Due to Enzyme Therapy After Complete Transaction of the Spinal Cord, 1965, ZH EKSP KLIN Med, 5(3): 3-13.

Smiseth et al., Effect of Hyaluronidase on Substrate Exchange and Blood Flow in the Ischaemic Myocardium of the Dog, 1982, Clinical Physiology, 2(1):39-50.

Rikuo Daichi, Text Book of Physiology, 2000, Third Edition, 81.

Curinga et al., Mammalian-Produced Chondroitinase AC Mitigates Axon Inhibition by Chondroitin Sulfate Proteoglycans, Journal of Neurochemistry, 2007, 102:275-288.

Crespo et al., How does Chondroitinase Functional Recovery in the Damaged CNS?, Experimental Neurology, 2007, 206:159-171.

Fawcett et al., The glial scar and central nervous system repair, 1999, Brain Res. Bull. 49(6):377-391.

Bradbury et al., Chondroitinase ABC promotes functional recovery after spinal cord injury, 2002, Nature 416:636-640.

Hoffman et al., Chondroitin Sulfates, 1958, Federation Proc. 17:1078-1082.

Yamagata et al., Purification and Properties of Bacterial Chondroitinases and Chondrosulfatases, 1968, J. Biol. Chem. 243(7):1523-1535.

Michelacci et al., Isolation and characterization of an induced Chondroitinase ABC, 1987, Biochem. Biophys. Acta 923:291-301.

Broach et al., Experimental Manipulation of Gene Expression, M. Inouye ed., Academic Press, 1983, New York, pp. 83-117.

Sambrook et al., Molecular Cloning, $2^{nd}$ ed., Cold Spring Harbor Laboratory Press, 1989 Ch. 16 and 17.

Sambrook et al., Molecular Cloning, $2^{nd}$ ed., Cold Spring Harbor Laboratory Press, 1989 (TOC).

Ben-Bassat et al., Processing of the Initiation Methionine from Proteins: Properties of the *Escherichia coli* Methionine Aminopeptidase and Its Gene Structure, 1987, J. Bacteriol. 169(2):751-757.

Miller et al., N-terminal methionine-specific peptidase in *Salmonella typhimurium*, 1987, PNAS 84:2718-2722.

Hou et al., Endotoxin Removal by Anion-Exchange Polymeric Matrix, 1990, Biotech. Appl. Biochem. 12:315-324.

Zuo et al., Degradation of Chondroitin Sulfate Proteoglycan Enhances the Neurite-Promoting Potential of Spinal Cord Tissue, 1998, Exp. Neurol. 154(2):654-662.

Zuo et al., Regeneration of Axons after Nerve Transaction Repair is Enhanced by Degradation of Chondroitin Sulfate Proteoglycan, 2002, Exp. Neurol. 1763(1):221-228.

Krekoski et al., Axonal Regeneration into Acellular Nerve Grafts is Enhanced by Degradation of Chondroitin Sulfate Proteoglycan, 2001, J. Neurosci. 15:21(16):6206-6213.

Blight et al., Animal models of spinal cord injury, 2002, Top Spinal Cord Inj. Rehabi. 6(2):1-13.

Kwon et al., Animal Models Used in Spinal Cord Regeneration Research, 2002, Spine 27(14):1504-1510.

Hirschberg et al., Inflammation after axonal injury has conflicting consequences for recovery of function: rescue of spared axons is impaired but regeneration is supported, J. Neuroimmunol. 1994, 50(1):9-16(Abstract).

Hamai et al., Two Distinct Chondroitin Sulfate ABC Lyases, 1997, J. Biol. Chem. 272(14):9123-9130.

Michelacci et al., Chondroitinase C from *Flavobacterium haparinum*, 1976, J. Biol. Chem. 251(4):1154-1158.

Korn, 1957, The Degradation of Heparin by Bacterial Enzymes, J. Biol. Chem. 226:841-844.

Martinez et al., Purification and Properties of the Enzyme Chondroitinase, 1959, J. Biol. Chem. 234(9):2236-2239.

Chau at al. "Chonciroltinase ABC Enhances Axonal Regrowth Through Schwann Cell-seeded Guidance Channels After Spinal Cord injury" Nov. 20, 2003 *FASEB J.* 18(1):1-24 (XP003008297).

Dimayuga at al, "The Neuregulin GGF2 Attenuates Free Radical Release from Activated Microglial Cells" Mar. 2003, *J. Netiroim.* 136(1-2):67-74 (XP002651543).

European Search Report for EP11152628 dated Jul. 21, 2011.

European Search Report for EP10184697 dated Jul. 12, 2011.

Grandpre et al, "Nogo-66 Receptor Antagonist Peptide Promotes Axonal Regeneration" May 30, 2002, *Nature* 417(6888):547-551 (XP002651544).

Hunt et al. "The Nogo Receptor, Its Ligands and Axonal Regeneration in the Spinal Cord; a Review" Feb. 2002, *J. Neurocytology* 31(2):93-120 (XP002651545).

Roy et al. "Treatment with Recombinant Chondroitinases AC and B Permits Neuronal Outgrowth Over Inhibitory Chondroitin Sulfate Proteoglycans (CSPGs)" Nov. 7, 2002, *Society for Neuroscience Abstract Archives* 2000-2005 (Abstract) (XP009150388).

* cited by examiner

METHODS OF PURIFYING CHONDROITINASE AND STABLE FORMULATIONS THEREOF

CROSS REFERENCE TO RELATED APPLICATIONS

This application claims priority from U.S. Provisional Application No. 60/572,030 filed May 18, 2004 entitled "Process of Purification of Chondroitinase," and from U.S. Provisional Application No. 60/621,882 entitled "cABCI Characterization and Formulation" filed Oct. 25, 2004, the contents of which are incorporated herein by reference in their entireties.

FIELD OF THE INVENTION

One aspect of the present invention relates to a stable formulation of chondroitinase. Another aspect of the present invention relates to methods of purifying chondroitinase.

BACKGROUND

Proteoglycans, major constituents of the extracellular matrix, are known to be present in large amounts in glial scar tissue and to inhibit recovery following spinal cord injuries (Fawcett & Asher, 1999). Enzymes that are capable of digesting glial scar tissue are an important target for the development of spinal cord injury (SCI) therapeutics. Chondroitinase ABCI (EC 4.2.2.4; cABCI) is a bacterial enzyme that catalyzes the digestion of sulfated chondroitin and dermatan side chains of proteoglycans. This enzyme has been shown to promote functional recovery after spinal cord injury (Bradbury et al., 2002; Caggiano et al., 2005).

The spinal cord is made up of nerve fibers. Damage to the central nervous system, including the spinal cord, results in a loss of function. Depending upon the type of injury to the central nervous system, the loss of function may manifest itself in loss of sensory, motor or autonomic function or a combination thereof. Sensory functions include the ability to feel sensations, like pain. Motor functions include the ability to voluntarily move your body. Autonomic functions include involuntary body functions, for example the ability to sweat and breathe.

The most common types of spinal cord injuries (SCI) include contusions (bruising of the spinal cord) and compression injuries (caused by prolonged pressure on the spinal cord). In contusion injuries, a cavity or hole often forms in the center of the spinal cord. Unlike nerve cells, or neurons of the peripheral nervous system (PNS), neurons of the central nervous system (CNS) do not regenerate after injury.

Spinal cord injury can be characterized by contusion of the neural tissue with a resultant decrease or loss of the ability of nerve tissue to properly transmit nerve impulses. The usual cause is due to an impact injury of some nature, but it may also occur during the manipulation of the spinal cord in certain surgical procedures. After a spinal cord injury in the adult mammal, the inability of axons to regenerate may lead to loss of sensation, loss of motor function and/or loss of autonomic function, as well as permanent paralysis. One reason that neurons fail to regenerate is their inability to traverse the glial scar that develops following a spinal cord injury. The injury-induced lesion will develop glial scarring, which contains extracellular matrix molecules including chondroitin sulfate proteoglycans (CSPGs). CSPG inhibit nerve tissue growth in vitro and nerve tissue regeneration at CSPGs rich regions in vivo.

A number of molecules, and specified regions thereof, have been implicated in the ability to support the sprouting of neurites from a neuronal cell, a process also referred to as neurite outgrowth. The term neurite refers to both axon and dendrite structures. The process of sprouting neurites is essential in neural development and regeneration, especially after physical injury or disease has damaged neuronal cells. Neurites elongate profusely during development both in the central and peripheral nervous systems of all animal species. This phenomenon pertains to both axons and dendrites.

Various polypeptides, especially cell adhesion molecules (CAMs), have been known to promote neural cell growth. While early efforts in this area of research concentrated on the adhesion-promoting extracellular matrix protein fibronectin (FN), other polypeptides have also been found to promote neural growth. For example, U.S. Pat. No. 5,792,743 discloses novel polypeptides and methods for promoting neural growth in the CNS of a mammal by administering a soluble neural CAM, a fragment thereof, or a Fc-fusion product thereof. U.S. Pat. No. 6,313,265 discloses synthetic polypeptides containing the pharmacologically active regions of CAMs that can be used in promoting nerve regeneration and repair in both peripheral nerve injuries as well as lesions in the CNS. While helpful, the use of regenerative proteins alone may not be sufficient to effect repair of a damaged nervous system.

During approximately the past two decades, knowledge of cell adhesion and migration in extracellular matrices (ECMs) at the molecular level has expanded rapidly. The action of enzymes and other polypeptides which degrade components of the extracellular matrix and basement membranes may facilitate the events of neural repair by a variety of mechanisms, including the release of bound cytokines and by increasing the permeability of the matrix, thereby enhancing the mobility of mediator molecules, growth factors and chemotactic agents, as well as the cells involved in the healing process. For example, U.S. Pat. No. 5,997,863 discloses the use of glycosaminoglycans to manipulate cell proliferation and promote wound healing.

Components of the inhibitory CSPGs have been identified as the glycosaminoglycans, chondroitin sulfate (CS) and dermatan sulfate (DS). Removal of these inhibitory molecules would allow neurites to regenerate and reinnervate an area after physical injury or disease, as well as to allow for the recovery of sensory, motor and autonomic functions.

Previous studies have found that chondroitinases can lyse and degrade CSPGs including, CS and DS. One study found that chondroitinase ABC removed glycosaminoglycan (GAG) chains in and around lesioned areas of rat CNS in vivo. The degradation of GAGs promoted expression of a growth-associated protein, GAP-43, indicating an increase in the ability of treated cells to regenerate. However, this growth-associated protein is associated with regeneration in peripheral, but not central, nerve injuries.

Chondroitin sulfates (CS) are sulfated polysaccharides in linear chains of a repeated dissacharides. They range in molecular weight from about 10,000 to over 100,000 Da. Chondroitin sulfate substrates exist in different isomers designated by the appended letters A, B, and C (Hoffman et al., 1958). The repeating units are composed of uronic acid (GlcA or IdoA) and galactosamine, and are called galactosaminoglycans, and are one example of the glycosaminoglycans, typically abbreviated as GAG. Although these GAG chain species have different repeating disaccharide regions, they are covalently bound through the so-called linkage region tetrasaccharide sequence (see below) to the serine residue in the GAG attachment consensus sequence (Glu/Asp-X-Ser- Gly) of respective core proteins. Chondroitin A and C sulfates (ChS-A, ChS-C) are the most abundant GAGs and are found in cartilage, bone and heart valves. Chondroitin B (ChS-B, or, alternatively, dermatan sulfate) is expressed mostly in skin, blood vessels, heart valves.

When chondroitinase bacterial preparations were characterized against different chondroitin sulfate (ChS) substrates, a series of distinct chondroitinases were discovered: chondroitinase AC that degrades mostly chondroitin A (ChA) and chondroitin C (ChC) (Yamagata et al., 1968), chondroitinase B that degrades chondroitin (ChB) (Michelacci and Deitrich, 1976), chondroitinase C that acts mostly on ChC (Michelacci Y M & Dietrich C P, 1976) and chondroitinase ABC exhibits specificity against all three substrates—ChS-A, ChS-B and ChS-C (Yamagata et al., 1968, Michelacci et al., 1987).

SUMMARY OF THE INVENTION

One aspect of the present invention provides stable formulations comprising chondroitinase and a buffer, preferably a sodium phosphate buffer. In one embodiment, a formulation comprising chondroitinase ABCI and about 100 mM sodium phosphate is provided.

Another aspect of the present invention provides methods of purifying chondroitinase. In one embodiment, the method of purifying chondroitinase comprises extracting the chondroitinase from cells, separating the chondroitinase from the extract, preferably using cation exchange chromatography, removing contaminants and impurities, preferably using gel filtration chromatography, and removing endotoxin, preferably using anion-exchange. The method may further comprise dialysis. The method may also further comprise drying. In a preferred embodiment, the chondroitinase is chondroitinase ABCI. In another preferred embodiment, the chondroitinase is chondroitinase AC.

Generally, the cells are suspended in a buffer solution containing a surface active agent and sonicated. The chondroitinase is then captured or separated from the extract mixture, preferably by passing the extract through a cation exchange column. Contaminants and impurities are removed from the captured chondroitinase, preferably by gel filtration. Endotoxins are removed from the chondroitinase sample, preferably by an anion exchange column. In one embodiment, the chondroitinase sample may be dialyzed, preferably using a volatile buffer. The chondroitinase may be further processed by drying or lyophilization. In an embodiment, the chondroitinase is chondroitinase ABC. In further embodiment the chondroitinase is chondroitinase AC. In a further embodiment the chondroitinase is a recombinant chondroitinase.

Another aspect of the invention provides a recombinant expression vector comprising a chondroitinase ABCI with a sequence of SEQ ID NO: 1. Another embodiment provides a recombinant expression vector comprising a chondroitinase ABCI with a sequence of SEQ ID NO: 2.

DESCRIPTION OF THE DRAWINGS

In part, other aspects, features, benefits and advantages of the embodiments of the present invention will be apparent with regard to the following description, appended claims and accompanying drawings where:

FIG. 2A. Purification of chondroitinase ABCI A280 profile of S200 column.

FIG. 4A Freezing/Thawing: Red—control; Blue—1 cycle; Green—2 cycles; Purple—3 cycles; FIG. 4B Exposure to $H_2O_2$: Red—control; Blue—0.5 mM; Green—5 mM; Purple—20 mM; FIG. 4C Continuous vortexing: Red—control; Blue—5 min; Green—20 min; Purple—60 min; FIG. 4D UV exposure: Red—control; Blue—40 min; Green—1 hr; Purple—2 hr; FIG. 4E Thermal (37° C.) stress: Red—control; Blue—1 hr; Green—4 hr; Purple—20 hr.

DETAILED DESCRIPTION

Figure 1:
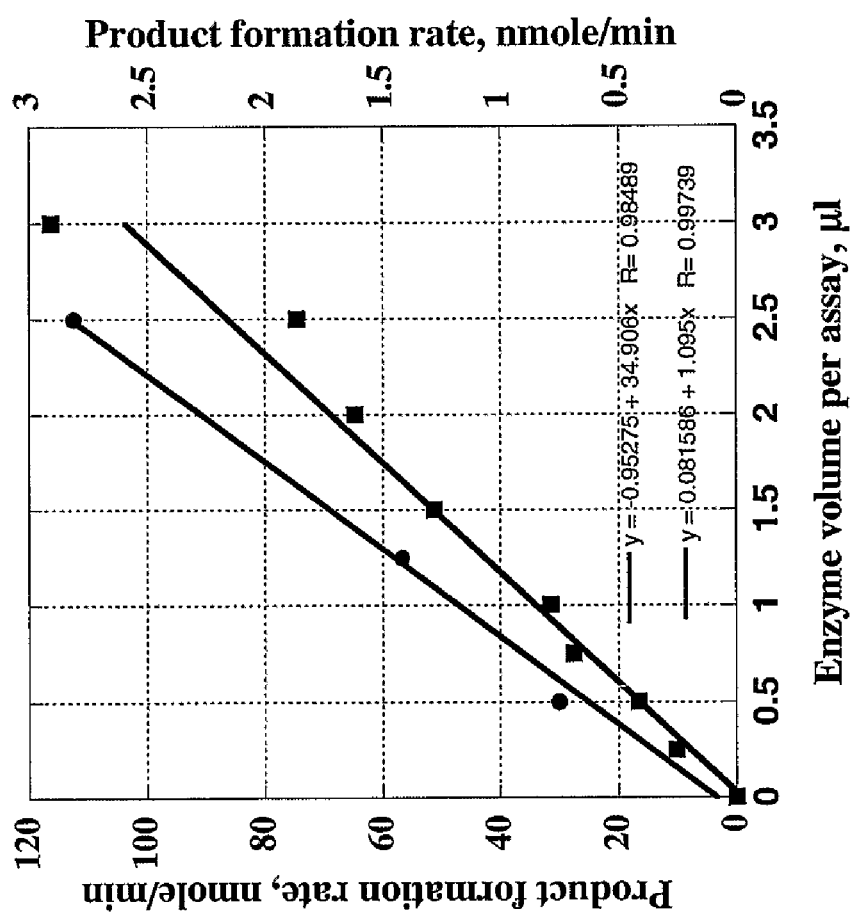
FIG. 1. Linear range for product formation rates in cABCI activity assay.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the protein. Moreover, the phrase "derived from", with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively treat an injury to the central nervous system. For example, a therapeutic compound comprising a therapeutically effective amount of chondroitinase which may be purified by a method of the present invention and formulated to provide a stable, active enzyme, is sufficient to degrade the CSPGs of the lesioned area of the spinal cord or an amount sufficient to restore, in whole or in part, motor, sensory or autonomic function of the mammal and may result in a regeneration of neurons in a central nervous system, such as by promoting axonal growth into an injured area.

The term "vector" refers to a vehicle which can transport the nucleic acid molecules. The nucleic acid molecules encoding the chondroitinase polypeptide are covalently linked to the vector nucleic acid. With this aspect of the invention, the vector can be a plasmid, single or double stranded phage, a single or double stranded RNA or DNA viral vector, or artificial chromosome, such as a BAC, PAC, YAC, OR MAC.

Chondroitinase as used herein include, but are not limited to, chondroitinase ABCI, chondroitinase ABCII, chondroitinase AC, chondroitinase B or mammalian enzymes with chondroitinase-like activity such as Hyal1, Hyal2, Hyal3, Hyal4 and PH2O.

Chondroitinase may be obtained from a microorganism that naturally expresses a chondroitinase; for example, but not limited to, *E. coli, Proteus vulgaris* or from the expression of a recombinant protein in a host cell. The host cell can be a prokaryotic cell (such as *E. coli*) or a eukaryotic cell (such as yeast, a mammalian cell or an insect cell).

In one embodiment of the invention, a recombinant chondroitinase ABCI from *Proteus vulgaris* was over-expressed in *E. coli*. The primary sequence of this protein is shown below:

(SEQ ID NO: 1)

*ATSNPAFDPKNLMOSEIYHFAQNNPLADILTLSDKRSIMGNQSLLWKWKG*

*GSSFTLHKKLIVPTDKEASKAWGRSSTPVFSFWLYNEKPIDGYLTIDFGEKLISTSEAQ*

*AGFKVKLDFTGWRTVGVSLNNDLENREMTLNATNTSSDGT*

QDSIGRSLGAKVDSIRFKAPSNVSQGEIYIDRIMFSVDDARYQW

SDYQVKTRLSEPEIQFHNVKPQLPVTPENLAAIDLIRQRLINEFVGGEKE

TNLALEENISKLKSDFDALNटHTLANGGTQGRHLITDKQIIIYQPENLNS

QDKQLFDNYVILGNYTTLMFNISRAYVLEKDPTQKAQLKQMYLLMTKHLL

DQGFVKGSALVTTHHWGYSSRWWYISTLLMSDALKEANLQTQVYDSLLWY

SREFKSSFDMKVSADSSDLDYFNTLSRQHLALLLLEPDDQKRINLVNTFS

HYITGALTQVPPGGKDGLRPDGTAWRHEGNYPGYSFPAFKNASQLIYLLR

DTPFSVGESGWNSLKKAMVSAWIYSNPEVGLPLAGRHPLNSPSLKSVAQG

YYWLAMSAKSSPDKTLASIYLAISDKTQNESTAIFGETITPASLPQGFYA

FNGGAFGIHRWQDKMVTLKAYNTNVWSSEIYNKDNRYGRYQSHGVAQIVS

NGSQLSQGYQQEGWDWNRMPGATTIHLPLKDLDSPKPHTLMQRGERGFSG

TSSLEGQYGMMAFDLIYPANLERFDPNFTAKKSVLAADNHLIFIGSNINS

SDKNKNVETTLFQHAITPTLNTLWINGQKIENMPYQTTLQQGDWLIDSNG

NGYLITQAEKVNVSRQHQVSAENKNRQPTEGNFSSAWIDHSTRPKDASYE

YMVFLDATPEKMGEMAQKFRENNGLYQVLRKDKDVHIILDKLSNVTGYAF

YQPASIEDKWIKKVNKPAIVMTHRQKDTLIVSAVTPDLNMTRQKAATPVT

INVTINGKWQSADKNSEVKYQVSGDNTELTFTSYFGIPQEIKLSPLP, wherein bolded and underlined residues indicate residues that do not correlate with those within the GeneBank sequences and italicized residues indicate a peptide sequence that was reported to be cleaved from the processed enzyme (Khandke, 1996).

In another embodiment, a recombinant chondroitinase can be produced from the amino acid sequence of the processed enzyme having the sequence:

(SEQ ID NO: 2)
QDSIGRSLGAKVDSIRFKAPSNVSQGEIYIDRIMFSVDDARYQWSDYQVK

TRLSEPEIQFHNVKPQLPVTPENLAAIDLIRQRLINEFVGGEKETNLALE

ENISKLKSDFDALNTHTLANGGTQGRHLITDKQIIIYQPENLNSQDKQLF

DNYVILGNYTTLMFNISRAYVLEKDPTQKAQLKQMYLLMTKHLLDQGFVK

GSALVTTHHWGYSSRWWYISTLLMSDALKEANLQTQVYDSLLWYSREFKS

SFDMKVSADSSDLDYFNTLSRQHLALLLLEPDDQKRINLVNTFSHYITGA

LTQVPPGGKDGLRPDGTAWRHEGNYPGYSFPAFKNASQLIYLLRDTPFSV

GESGWNSLKKAMVSAWIYSNPEVGLPLAGRHPLNSPSLKSVAQGYYWLAM

SAKSSPDKTLASIYLAISDKTQNESTAIFGETITPASLPQGFYAFNGGAF

GIHRWQDKMVTLKAYNTNVWSSEIYNKDNRYGRYQSHGVAQIVSNGSQLS

QGYQQEGWDWNRMPGATTIHLPLKDLDSPKPHTLMQRGERGFSGTSSLEG

QYGMMAFDLIYPANLERFDPNFTAKKSVLAADNHLIFIGSNINSSDKNKN

VETTLFQHAITPTLNTLWINGQKIENMPYQTTLQQGDWLIDSNGNGYLIT

QAEKVNVSRQHQVSAENKNRQPTEGNFSSAWIDHSTRPKDASYEYMVFLD

ATPEKMGEMAQKFRENNGLYQVLRKDKDVHIILDKLSNVTGYAFYQPASI

EDKWIKKVNKPAIVMTHRQKDTLIVSAVTPDLNMTRQKAATPVTINVTIN

GKWQSADKNSEVKYQVSGDNTELTFTSYFGIPQEIKLSPLP.

Expression of a recombinant chondroitinase gene can be produced by ligating a nucleic acid encoding a chondroitinase protein, or a portion thereof, into a vector suitable for expression in either prokaryotic cells, eukaryotic cells, or both. Procedures for ligation are well known to those of ordinary skill in the art. Expression vectors for production of recombinant forms of the subject chondroitinase polypeptides include plasmids and other vectors. For instance, suitable vectors for the expression of a chondroitinase polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in *Experimental Manipulation of Gene Expression*, ed. M. Inouye Academic Press, p. 83, incorporated by reference herein). These vectors can replicate in E. coli due to the presence of the pBR322 origin of replication, and in S. cerevisiae due to the replication determinant of the yeast 2 micron plasmid. In addition, drug resistance markers such as ampicillin may be used.

In another embodiment, a chondroitinase polypeptide is produced recombinantly utilizing an expression vector generated by subcloning the coding sequence of one of the chondroitinase proteins represented in SEQ ID NO: 1 or SEQ ID NO: 2.

Mammalian expression vectors may contain prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRS-Vneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press: 1989) Chapters 16 and 17, there references are incorporated herein.

In some instances, it may be desirable to express the recombinant chondroitinase polypeptide by the use of an insect expression system such as the baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The expression vectors listed herein are provided by way of example only and represent the well-known vectors available to those of ordinary skill in the art that may be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989, the text of which is incorporated herein.

When it is desirable to express only a portion of a chondroitinase protein, such as a form lacking a portion of the N-terminus, i.e. a truncation mutant which lacks the signal peptide, it may be necessary to add a start codon (ATG, which encodes the amino acid methionine) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) *J. Bacteriol.* 169:751-757) and *Salmonella typhimurium* and its in vitro activity has been demonstrated on recombinant proteins (Miller et al. (1987) *PNAS* 84:2718-1722). Therefore, removal of an N-terminal methionine, if desired, can be achieved either in vivo by expressing chondroitinase-derived polypeptides in a host which produces MAP (e.g., E. coli or CM89 or S. cerevisiae), or in vitro by use of purified MAP.

Expression vectors contain cis-acting regulatory regions that are operably linked in the vector to the chondroitinase nucleic acid such that transcription of the nucleic acid molecules is allowed in a host cell.

The recombinant host cells are prepared by introducing the vector constructs into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

As is known in the art, chondroitinase polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The chondroitinase polypeptide may be secreted and isolated and from a mixture of cells and medium containing the recombinant chondroitinase polypeptide. Aspects of the invention described herein provide purification methods wherein the chondroitinase is isolated in a pure form that is more stable and active then those methods currently used.

Alternatively, the peptide may be retained cytoplasmically by removing the signal peptide sequence from the recombinant chondroitinase gene and the cells harvested, lysed and the protein isolated by the purification methods described herein.

According to one aspect of the invention, the process of purifying chondroitinase comprises the following steps: 1) extracting the enzyme from a cell, 2) separating the crude cell extract using cation-exchange chromatography, 3) further separating the extract by a gel filtration chromatography, and 4) removing endotoxin through an anion-exchange membrane to produce a purified chondroitinase, which exhibits high activity relative to chondroitinase purified by conventional methods.

Extraction of chondroitinase from cells can be more effective by using a buffer solution to which a surfactant is added. A surfactant is a surface active agent that has solubilizing tendencies and that contains groups of opposite polarity. These agents may be used to disrupt the integrity of a cell. Thus, a surfactant may be used to extract an enzyme from a cell. Any surfactant which can promote the extraction of chondroitinase from a cell can be used in the present invention, preferably the surfactant is a nonionic surfactant.

Nonionic surfactants which can be used include, but are not limited to, polyoxyethylene alkyl ethers, polyoxyethylene p-t-octylphenyl ethers, polysorbate, and the like. Emulgen-type surfactants, Liponox-type surfactants, Brij-type surfactants, and the like are given as specific examples of polyoxyethylene alkyl ethers. Commercially available surfactants among these are Emulgen 120, Emulgen 109P, Liponox DCH, Brij 35, 78, 76, 96, 56, 58, 98, Nikkol BL-9EX, BL-21, BL-25, and the like. Given as specific examples of polyoxyethylene p-t-octylphenyl ethers are Triton-type surfactants, Nonidet P40-type surfactants, Igepal/CA-type surfactants, Polytergent G, Neutronyx-type surfactants, Conco-type surfactants, and the like. Among these types of surfactants, Triton X-100, X-45, X-114, X-102, X-165, X-305, X-405, Nonidet P-40, Igepal CA-630, Neutronyx 605, Conco NIX-100, and the like are commercially available. Tween-type surfactants, Emasol-type surfactants, Sorbester-type surfactants, Crill-type surfactants, and the like are given as specific examples of polysorbates. Sorbitan mono-9-octadecanoate poly(oxy-1,2-ethanediyl) derivatives, commercially available as Tween 80 are preferred as polysorbate and the like.

Of the above surfactants, Triton X surfactants are preferred, including but not limited to Triton X-114. Generally, the detergent such as, but not limited to, Triton X, can be added to the sample of cells to be extracted. In one embodiment of the invention, the concentration of the detergent can range from about 0.1% to about 10% (v/v), preferably in the range of about 0.1% to about 3% (v/v), or more preferably in the range of about 0.2% to about 2%.

In one embodiment of the invention, the process of extraction may also involve sonication. Sonication involves the use of sound waves to disrupt fragile cells (made fragile, for example, by exposure to a surfactant, such as Triton X). This results in dispersing and disrupting the cells such that the integrity of the cell is further destroyed, thereby causing the release of intracellular components. Sonication may involve either or both a pulsed or continuous exposure to sound waves. For example, to sonicate the cells, a small (micro) probe can be used. The sonicator can be set to pulse (not continuous). In another embodiment, the sonicator can be set to continuous. In a further embodiment, the sonication step may use a combination of pulsed and continuous sonication. In one embodiment, the cell suspension may be sonicated with 10 short burst of 10 seconds followed by intervals of 30 seconds for cooling. The cell suspension may be kept on ice during sonication to avoid overheating of the sample constituents. Following sonication the cell debris may be removed by centrifugation. Other methods of sonication may be employed, as readily determined by those skilled in the art, depending on the cell type being disrupted.

In another embodiment, enzyme extraction may also involve polytron homogenization. This process will mechanically grind up the surfactant treated cells, therein disrupting cell integrity, and releasing cell components into a solution for further purification. Generally, the sample is maintained on ice to prevent or limit any heating of the sample. The sample may be homogenized for about 30 seconds, or until the cell clumps have been dispersed. Methods for performing polytron homogenization are well known in the art.

The chondroitinase may be captured from the cell extract using ion exchange chromatography. In ion exchange chromatography, charged substances are separated using column materials that carry an opposite charge. Two exchanger types are differentiated: basic (positively charged) and acidic (negatively charged). The ion exchanger types can be further divided into weakly basic or acidic or strongly basic or acidic. With strongly basic or acidic materials all functional groups are generally present in the ionized form. For example, the quaternary amino groups ($R_3N^+$) are positively charged, while the sulfonic acid groups ($SO_3^-$) are negatively charged. The weakly basic types and weakly acidic types of ion exchange columns also exist. The weakly basic types are generally secondary and tertiary amino functional groups; the weakly acidic types are generally carboxyl functional groups.

Many proteins can be separated as polyanions (pH>pI) or as polycations (pH<pI). The most common ion exchanger groups include, but are not limited to, imethylammoniumethyl (anion), diethylaminoethyl (anion), dimethylaminoethyl (anion), carboxy (cation), carboxyalkyl (cation), sufoisobutyl (cation), sulphoalkyl (cation), sulphopropyl (cation) and sulfoethyl (cation).

To capture the enzyme from the cell extract, the extract obtained may be subjected to cation exchange chromatography. Using a cation exchange resin produces a chondroitinase with increased activity and purity compared to the crude lysate. Weak or strong cation exchange resins may be used, for example, but not limited to, cation exchange resins having a carboxyalkyl group and a sulfoalkyl or sulphopropyl group, respectively. Other cation exchange resins are well known in the art (see above).

Thus, in one embodiment of the invention the enzyme may be captured from the cell extract by loading the sample onto the cation exchange chromatography, washing of the cation exchanger, in which the cell components other than chondroitinase are washed out by increasing the ion strength and/or by pH changes, i.e. under cation-exchange chromatography conditions; and elution of the chondroitinase sample by a further increase in the ion strength and/or by a pH change.

Buffers used in cation exchange chromatography include, but are not limited to those listed in Table 1.

TABLE 1

Cation Exchange Chromatography Buffers

| Molecule | pKa | dpKa/degree C. | Counter ion |
|---|---|---|---|
| Maleic acid | 2.00 | | sodium |
| Malonic acid | 2.88 | | sodium |
| citric acid | 3.13 | −0.0024 | sodium |
| lactic acid | 3.81 | | sodium |
| formic acid | 3.75 | 0.0002 | sodium or lithium |
| ZZbutaneandioic acid | 4.21 | −0.0018 | sodium |
| acetic acid | 4.76 | 0.0002 | sodium or lithium |
| malonic acid | 5.68 | | sodium or lithium |
| phosphate | 7.20 | −0.0028 | sodium |
| HEPES | 7.55 | −0.0140 | sodium or lithium |
| BICINE | 8.35 | −0.0180 | sodium |

Removal of aggregates and low molecular weight contaminants and impurities may be carried out through various filtration methods including, for example, gel filtration or size exclusion chromatography. Commercially available examples of gel filtration are Sephadex and Sephacryl.

Gel filtration chromatography is a separation based on size. It is also called molecular exclusion or gel permeation chromatography. In gel filtration chromatography, the stationary phase consists of porous beads with a well-defined range of pore sizes. The stationary phase for gel filtration is said to have a fractionation range, meaning that molecules within that molecular weight range can be separated.

Thus, proteins that are small enough can fit inside all the pores in the beads and are said to be included. These small proteins have access to the mobile phase inside the beads as well as the mobile phase between beads and elute last in a gel filtration separation. Proteins that are too large to fit inside any of the pores are said to be excluded. They have access only to the mobile phase between the beads and, therefore, elute first. Proteins of intermediate size are partially included—meaning they can fit inside some but not all of the pores in the beads. These proteins will then elute between the large ("excluded") and small ("totally included") proteins.

Another contaminant that may be present in the cell lysate preparation is endotoxin. Endotoxin is a common toxic contaminant in biological systems. It is important to sufficiently remove endotoxin which is a component of the cell wall of bacteria. Endotoxin is a lipopolysaccharide in the cell wall of most gram-negative bacteria such as E. coli. Endotoxin included in proteins is known to cause symptoms of high fever, endotoxin shock, and inflammation even in a very small amount. Since bacterial extracts may be highly contaminated with endotoxin, embodiments of the invention may include an endotoxin removal step in a purification process. Various methods may be employed for the removal of endotoxin such as, but not limited to, cation exchange chromatography, anion exchange chromatography, affinity chromatography, ultrafiltration, and phase-separation using a surfactant.

In one embodiment of the invention, the endotoxin is removed using an anion exchange column. Examples of anion exchange chromatography include, but are not limited to, Q-membrane, a quaternary amine; and diethylaminoethane (DEAE) resin. Buffers used in anion exchange chromatography include, but are not limited to those illustrated in Table 2.

TABLE 2

Anion Exchange Chromotography Buffers

| Molecule | pKa | dpKa/degree C. | Counter ion |
|---|---|---|---|
| N-methyl piperazine | 4.75 | −0.015 | chloride |
| piperazine | 5.68 | −0.015 | chloride or formate |
| L-histidine | 5.96 | | chloride |
| bis-Tris | 6.46 | −0.017 | chloride |
| bis-Tris propane | 6.80 | | chloride |
| triethanolamine | 7.76 | −0.020 | chloride or acetate |
| Tris | 8.06 | −0.028 | chloride |
| N-methyl-diethanolamine | 8.52 | −0.028 | chloride |
| diethanolamine | 8.88 | −0.025 | chloride |
| 1,3-diaminopropane | 8.64 | −0.031 | chloride |
| ethanolamine | 9.50 | −0.029 | chloride |
| piperazine | 9.73 | −0.026 | chloride |
| 1,3-diaminopropane | 10.47 | −0.026 | chloride |
| piperidine | 11.12 | −0.031 | chloride |
| phosphate | 12.33 | −0.026 | chloride |

Partitioning may occur at various steps of the process, preferably during purification prior to gel filtration. Filtration through Q membranes is another alternative for endotoxin cleaning step. In one embodiment, Q membrane filtration may be employed using a pH of pH 5.5 in 20 mM NaAcetate and 100 mM NaCl. According to K. C. Hou and R. Zaniewski, Biotech. Appl. Biochem. 12, 315-324, 1990, these pH and salt conditions are expected to remove in the range of about 70 to 85% endotoxin. In one embodiment a Q filtration process in a flowthrough collection mode yields greater than about 95% of chondroitinase. Q membrane filtration may be performed at various times during the process, including, for example, at the end of purification after gel filtration.

Thus, in one embodiment of the invention the removal of the endotoxin from the chondroitinase in the sample may include loading the sample onto the anion exchange chromatography, washing of the anion exchanger, in which the impurities are washed out by increasing the ion strength and/or by pH changes, i.e. under anion-exchange chromatography conditions; and elution of the chondroitinase sample by a further increase in the ion strength and/or by a pH change.

Dialysis is one of the most commonly utilized methods for transferring a biological sample, usually protein based, from one media to another. It is frequently necessary to remove salts or change the buffer after one step in the purification for the next step to work efficiently. This may be achieved by dialysis wherein the protein solution is kept in a semi-permeable membrane and placed in the buffer so that small molecules e.g. salts, can pass freely across the membrane whilst large molecules e.g. proteins, are retained. One embodiment of the present invention includes a dialysis step to further purify the chondroitinase. A volatile buffer, such as ammonium bicarbonate, pH 8.0 may be used for the dialysis step. Other buffers may also be used. The choice of buffer chosen should be one that is appropriate for the protein being dialyzed. Such buffers are well known in the art (for example, but not limited to, Tris based buffers, phosphate buffers, etc). The buffer used for dialysis may be any buffer that is able to maintain the appropriate pH in which to stabilize the protein being isolated.

For storage and distribution of the purified chondroitinase, the process of purifying the chondroitinase may further include the step of drying. The step of drying may involve conventional heat drying or more preferably, lyophilization or freeze drying.

Embodiments of the invention may include a method of monitoring the enzyme yields and purity profiles by reverse-phase HPLC is further provided. This may be performed following any or all of the steps in the purification process.

In one embodiment of the invention the final enzyme yield can be up to about 50 mg chondroitinase from 1 L cultured cells. In a further embodiment the final enzyme yield can be in the range of about 75 to 85 mg/l L of cells.

The purified chondroitinase of the present invention may be characterized by one or more of the following properties: enzyme activity, the pI, the substrate specificity, the rate of substrate catalysis, the inhibitory effect of divalent metal salts, the optimal storage buffer pH, the effects of various stress conditions, the optimal buffer and ionic strength, stabilization of the enzyme in various excipients, and the effect of enzyme concentration on thermal stability.

A chondroitinase ABCI was used as an example of a chondroitinase that can be purified and formulated according to the embodiments of the invention. The lyophilized purified chondroitinase ABCI was reconstituted and assayed for activity which was compared to activities of chondroitinase ABCI enzymes available from other sources. The activity of the chondroitinase ABCI enzyme of the present invention was a relatively high enzyme preparation. The activity of the purified chondroitinase ABCI is about 160 U/mg. The pI of the purified chondroitinase ABCI of the present invention is about 7.8 to about 8.0. The affinity of the purified chondroitinase ABCI is similar for chondroitin A, chondroitin B, and chondroitin C. The rate of catalysis of a substrate for the purified chondroitinase ABCI of the present invention is greater for chondroitin A then chondroitin C, which is greater then the rate of catalysis of chondroitin B.

Divalent metal salts may inhibit an activity of chondroitinase. For example, the purified chondroitinase ABCI may be inhibited by Zn, Ni and Co. Ca and Mg appear to be less inhibitory. Storage buffer pH does not affect the activity of the purified chondroitinase. In preferred embodiments, the storage buffer is pH 7.4, physiological pH.

While chondroitinase generally may be affected by various adverse conditions, the purified chondroitinase of the present invention does not appear to be affected by repeated freezing and thawing.

Various embodiments provide a stable formulation of the enzyme for both storage and administration. Generally, the chondroitinase of such stable formulations exhibit at least about 50% of activity at about 24 hours, preferably at least about 75% of activity, more preferably at least about 85% of activity. In another aspect of the invention, the formulations consistently provide stable chondroitinase activity.

In one embodiment, the chondroitinase is formulated in a phosphate buffer, preferably a sodium phosphate buffer with a concentration in the range of about 50 mM to about 1 M. A preferred embodiment is about 750 mM sodium phosphate. Another preferred embodiment is about 100 mM sodium phosphate. In a further embodiment the chondroitinase may be formulated in a sodium phosphate buffer that further comprises sodium acetate. Sodium acetate may be present in the range of 25 mM to about 75 mM. In a preferred embodiment the sodium acetate concentration is about 50 mM. In one embodiment a preferred formulation for administration is a chondroitinase in a buffer with a pH of about 7.4. Further embodiments of formulations for storage and administration are provided in the Examples described.

In further embodiment, a formulation comprising purified chondroitinase and a buffer comprising an increased ionic strength is provided. Embodiments wherein a formulation comprises an increased ionic concentration may increase stability of an enzyme formulation. For example, a preferred embodiment provides a formulation with about 1 M NaCl in sodium phosphate. The concentration of sodium phosphate may be about 50 mM. In a preferred embodiment, the chondroitinase storage concentration is below about 0.4 mg/ml.

In one embodiment, a chondroitinase ABC formulation comprises about 0.4 mg/ml of chondroitinase ABC in about 100 mM Na phosphate, at a pH of about 7.4 with a preferred substrate specificity for chondroitin A, B, and C about the same. In another embodiment, a formulation comprising a chondroitinase B with a purified chondroitinase ABC is provided.

In another embodiment, a chondroitinase AC purification is provided comprising the following steps: 1) extracting the enzyme from a cell, 2) separating the crude cell extract using cation-exchange chromatography, 3) further separating the extract by a gel filtration chromatography, and 4) removing endotoxin through an anion-exchange membrane to produce a purified chondroitinase AC. In an embodiment a purified chondroitinase AC is dialyzed into a volatile buffer, lyophilized and stored at −80° C. Example 12 describes one embodiment of a method of purification of a chondroitinase AC.

In one embodiment, reconstitution and about 4° C. storage in a buffer at about 0.1M sodium phosphate, pH 7.4, 50 mM sodium acetate is provided. In another embodiment, stabilizing buffer (for about 37° C. studies) at about 0.75M sodium phosphate, pH 7.4, 50 mM sodium acetate is provided. In another embodiment storage of chondroitinase is in the lyophilized form.

Chondroitinase activity can be stabilized by the addition of excipients or by lyophilization. Stabilizers include carbohydrates, amino acids, fatty acids, and surfactants and are known to those skilled in the art. Examples include carbohydrates such as sucrose, lactose, mannitol, and dextran, proteins such as albumin and protamine, amino acids such as arginine, glycine, and threonine, surfactants such as TWEEN® and PLURONIC®, salts such as calcium chloride and sodium phosphate, and lipids such as fatty acids, phospholipids, and bile salts.

The stabilizers are generally added to the protein in a ratio of 1:10 to 4:1, carbohydrate to protein, amino acids to protein, protein stabilizer to protein, and salts to protein; 1:1000 to 1:20, surfactant to protein; and 1:20 to 4:1, lipids to protein. Other stabilizers include high concentrations of ammonium sulfate, sodium acetate or sodium sulfate, based on comparative studies with heparinase activity. The stabilizing agents, preferably the ammonium sulfate or other similar salt, are added to the enzyme in a ratio of 0.1 to 4.0 mg ammonium sulfate/1 U enzyme.

Chondroitinase may be administered topically, locally or systemically. Topical or local administration is preferable for greater control of application. The chondroitinases, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing fatty acids, isotonizing agents, preservants, anesthetics, surfactants and the like, and are known to those skilled in the art. Specifically pharmaceutical carriers that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds. Pharmaceutical carriers may also be used in combination, such as polyethylene glycol and/or sucrose, or polyoxyethylene sorbitan fatty acid esters, polyoxyethylene sorbitan monooleate (20 E. O.) is particularly preferred. A treatment regimen according to the invention may be carried out by a means of administering, alone or a combination of thereof, chondroitinase ABCI, chondroitinase ABCII, chondroitinase AC and chondroitinase B or mammalian enzymes with chondroitinase-like activity such as Hyal1, Hyal2, Hyal3, Hyal4 and PH2O to the lesions of the injured area of the CNS. The mode of administration, the timing of administration and the dosage are carried out such that the functional recovery from impairment of the CNS is enhanced by the promotion of neurite outgrowth. The treatments of the present disclosure deliver an effective amount of chondroitinase ABCI purified according to the present invention alone or in combination with chondroitinase ABCII, chondroitinase AC and chondroitinase B or mammalian enzymes with chondroitinase-like activity such as Hyal 1, Hyal 2, Hyal 3, Hyal 4 and PH2O to the injured site.

The effective amount of chondroitinase can be administered in a single dosage, two dosages or a plurality of dosages. Although it is to be understood that the dosage may be administered at any time, in one embodiment, the dosage is administered within 12 hours after injury, or as soon as is feasible. In another embodiment, the dosage is administered to an injured mammal in one, two or a plurality of dosages; such dosages would be dependant on the severity of the injury and the amount of CSPGs present in the glial scarring. Where a plurality of dosages is administered, they may be delivered on a daily, weekly, or bi-weekly basis. The delivery of the dosages may be by means of catheter or syringe. Alternatively, the treatment can be administered during surgery to allow direct application to the glial scar.

As an example of a purified formulation of a chondroitinase a recombinant ABCI (cABCI) was purified and characterized using the methods of the present invention using the following parameters: temperature stability, enzyme characteristics, susceptibility to various stress conditions, degradation products; effects of different excipients on enzyme stability.

The following methods are used to illustrate the various embodiments of the present invention. The methods are exemplary methods and are not meant to limit the invention.

Activity assay. The enzymatic activity of cABCI was assayed according to a modified version from Hamai et al. (1997). 125 µl of reaction mixture containing 40 mM Tris, pH 8.0. 40 mM NaAcetate, 0.002% casein was incubated at about 37° C. for at least 3 min. After incubation, 1 mg/ml (final concentration) chondroitin C sulfate and 0.05-0.5 µg cABCI enzyme were added, the mixture was gently vortexed and then the product formation rate was monitored by the absorption at about 232 nm for about 45-90 sec. Calculations for substrate and product concentrations were based on MW of hexuronate residues equaling 521 and the molar extinction coefficient ($\epsilon^{232}$) for unsaturated hexuronate-6-sulfate at 232 nm of 5,500. When chondroitin A and B are used as substrates in the assay, the calculations for unsaturated hexuronate-4-sulfate products were done with MW equaling 503 and an $\epsilon^{232}$ of 5,100. Initial activity rates were calculated in nmole of disaccharide/min by fitting the collected data into a linear function. Specific enzyme activity was expressed in U/mg, where unit (U) is defined as µmole of product formed within 1 min. The linear range for measuring chondroitin degradation rate was wide as shown in FIG. 1.

Estimation of extinction coefficient. The extinction coefficient for different batches of cABCI was determined. Two different batches of purified chondroitinase ABCI were reconstituted in 20 mM sodium acetate, pH 5.5, 100 mM NaCl. Some samples contained 0.3M sucrose in the reconstitution buffer. Absorption at 280 nm and protein concentrations using modified Lowry protein assay measurements were taken for each sample. Estimation of extinction coefficient for cABCI is presented in Table 3 below.

TABLE 3

| cABCI sample | Extinction Coefficient | | |
|---|---|---|---|
| | A280 | Concentration, mg/ml | $0.1\%_{\epsilon 280}$ |
| Batch 5c-4° C. | 0.928 | 0.68 | 1.36 |
| Batch 5c-4° C. sucrose | 0.53 | 0.4 | 1.32 |
| Batch 5c-T$_{room}$ | 0.672 | 0.342 | 1.96 |
| Batch 5c-T$_{room}$ sucrose | 0.46 | 0.25 | 1.84 |
| Batch 5d | 1.81 | 0.98 | 1.84 |
| | | | Average 1.66 |

Extinction coefficient estimate for 0.1% cABCI solution was derived by dividing A280 by concentration (mg/ml). The averaged extinction coefficient (1.66) was used in further experiments for cABCI concentration measurements.

Size exclusion chromatography (SEC) characterization. Analytical SEC was used to characterize aggregation and conformation of the chondroitinase ABCI. Analytical SEC was performed using a Shodex KW-803, which has a separation range of about 50,000 to 150,000 Daltons (Da) and Shodex KW-804 columns, which has a separation range of about 100,000 to 600,000 Daltons (Da). The buffer for the mobile phase was 100 mM sodium phosphate, 50 mM NaCl, 0.5% betaine, pH 7.3. The analysis was done at flow rate 1 ml/min at ambient temperatures (approximately 22° C.).

Protein assay. To determine the protein concentration a modified Lowry protein assay (BioRad) and BCA (Pierce) were used according to supplier instructions.

SDS-PAGE. Proteins were separated on a 4-20% gradient SDS-PAGE precast minigel (BioRad) and electrophoresis was carried out at 200V in a minigel apparatus (BioRad). The gels were then stained with either Coomassie or Silver stain.

IEF-PAGE. IEF-PAGE was carried out to determine the pI value for chondroitinase ABCI in a 3-10 pH range using NOVEX IEF gels (Invitrogen) and run according to manufacturer's instructions using a NOVEX gel apparatus. The gels were stained with Colloidal Blue Coomassie.

Western blotting. The proteins were separated on SDS-PAGE- and then electroblotted onto nitrocellulose membrane by the tank-transfer method (BioRad) according to the manufacturer's instructions. The transfer buffer contained 25 mM Tris and 192 mM Glycine at pH 8.3, 1% SDS.

Oxyblot assay. Detection of carbonyl groups that are introduced into protein side chains by a site-specific mechanism was provided by OxyBlot Protein Oxidation Detection kit from Chemicon International. Specifically, the carbonyl groups in the protein side chains were derivatized by 2,4-dinitrophenylhydrazine (DNPH) to 2,4-dinitrophenylhydrozone (DNP-hydrozone). The samples were then blotted onto nitrocellulose. The membrane was then exposed to a DNP specific primary antibody. Following incubation with the primary antibody the membrane was incubated with an HRP-conjugated secondary antibody. The presence of the antibody complex was detected by chemiluminescence.

Cation-Exchange HPLC assay. cABCI oxidation products were analyzed using Dionex ProPac WCX-10 Cation Exchange column attached to Thermo Finnigan Chromatographic system consisting of Surveyor PDA detector, pump & autosampler. The enzyme was eluted with a NaCl gradient in 10 mM NaPhosphate buffer, pH 6.0. The detector's wavelength was set to 215 nm.

Size exclusion chromatography. Analytical size exclusion chromatography was performed through a KW-803 column (Showdex Inc.), which has a separation range of about 50 to 150,000, and a KW-804 column, which has a separation range of about 100,000-600,000, using HPLC (ESA Inc.) supplied with light-scattering (Wyatt Technology) and UV detector (Waters Co.). 100 mM NaPhosphate, pH 7.4 was used as a mobile phase.

Stress studies of cABCI. The lyophilized cABCI enzyme was reconstituted in a buffer of choice. The enzyme was allowed to reconstitute either on ice or at about 4° C. for several hours and insoluble material, if any, was removed by centrifugation at 14,000 g. Then 100 µl aliquots were subjected to different stress conditions, including but not limited to, temperature, continuous vortexing, freeze-thawing, UV light, hydrogen peroxide presence. Samples subjected to UV light were kept on ice during exposure to minimize any heating effect on the enzyme. Vortexing was done at about 4° C. Oxidation by hydrogen peroxide was tested by incubating samples with different hydrogen peroxide concentrations overnight at 4° C. Freeze-thawing cycles were executed on dry ice. Post-treatment samples were assayed for protein concentration by A280 readings, enzyme activity by spectrophotometry and further assessed by reducing and non-reducing SDS-PAGE, denatured IEF-PAGE, SEC and cation-exchange HPLC.

Formulation studies for cABCI. Since cABCI may be susceptible to heat inactivation, incubation at about 37° C. was also used as a stressor in formulation studies. The reconstituted cABCI samples were incubated overnight or longer in a 37° C. water bath with different additives and buffer components. After incubation, the samples were assayed for enzyme activity.

Example 1

Recombinant chondroitinase ABCI was overexpressed in E. coli and purified according to the following steps:

(i) enzyme extraction with Triton X-114/PBS and sonication from bacterial cell pellet;

(ii) SP cation-exchange chromatography in sodium acetate buffer at pH 5.5;

(iii) Sephacryl S200 gel filtration chromatography in sodium acetate buffer at pH 5.5;

(iv) filtration through Q anion-exchange membrane for endotoxin and DNA removal; and (v) dialysis into a volatile buffer (ammonium bicarbonate at pH 8.0). Optionally this step may be followed by lyophilization, or by any other methods of concentrating and removal of buffer (for example, sterile filtration followed by suspending in an appropriate formulation).

A recombinant chondroitinase ABCI was overexpressed in E. coli. A large portion of the enzyme was released into solution with non-ionic detergent and sonication. An SDS-PAGE, visualized with silver stain, of the detergent-soluble extract and detergent-insoluble pellet fractions from ABCI-overexpressing bacterial cells revealed a single large band running between size markers of about 75 kDa and 100 kDa.

Cation-exchange chromatography was used as a capture step in further purifications. CEX SP chromatography at about pH 5.5 in acetate buffer was effective for capturing chondroitinase ABCI from the bacterial cell extract. It was found that the enzyme was bound quantitatively and eluted from the SP column with relatively high purity and yield when Triton X-114, final concentration in the range of about 0.2-1%, detergent was used in the extraction buffer. SDS-PAGE analysis of chondroitinase ABCI start, flow-through and elution fractions (25% B) from SP column for Triton X-114 extract revealed that the chondroitinase ABCI was eluted. A Triton X-100-containing extract appeared to alter the chondroitinase ABCI charge characteristics resulting in poor capture, poor elution yields and low step purity.

Removal of endotoxin was achieved by two methods, specifically partitioning into Triton X-114 and Q anion exchange membrane filtration.

SDS-PAGE analysis of chondroitinase ABCI fractions during endotoxin removal step using Triton X-114 partitioning method detected a single large band in the absence of any background bands.

Filtration through Q membranes was employed for the endotoxin removal step. This method was tested at about pH 5.5. 20 mM NaAcetate, pH 5.5, 100 mM NaCl was found to be an effective buffer for endotoxin binding to Q membranes (according to K. C. Hou and R. Zaniewski, Biotech. Appl. Biochem. 12, 315-324, 1990, these pH and salt conditions are expected to remove approximately 75% endotoxin) and for minimizing cABCI losses during this step. Greater than 95% of the cABCI was collected in a flowthrough mode. This step was performed following gel filtration at the end of purification, as described below.

Gel filtration was used as a polishing step for chondroitinase ABCI. Examples of gel filtration that can be used include Sephacryl S200 and Sephacryl S300. Sephacryl S200 and Sephacryl S300 were tested for their efficacy in separating aggregates and low molecular weight contaminants. Two different elution buffers (Buffer 1:20 mM Tris at pH 8.0, 200 mM NaCl, 0.5% betaine and Buffer 2:20 mM sodium acetate at pH 5.5, 100 mM NaCl) for each gel were tested and found to work equally well. The chondroitinase ABCI was eluted with the expected retention times without substantial loss in sample.

Figure 2:
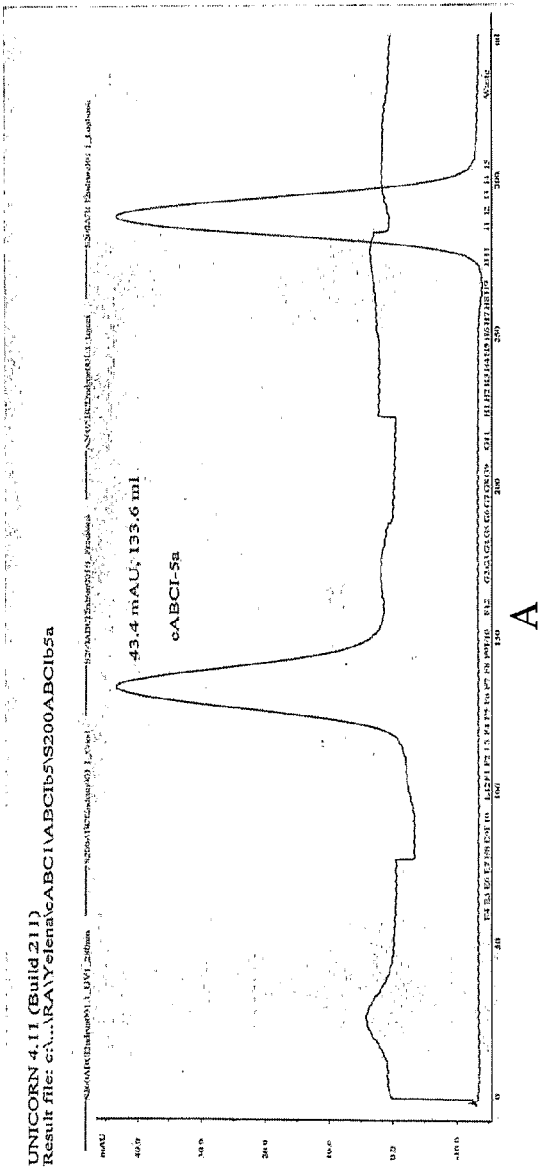
FIGS. 2 B & C: SDS-PAGE of chondroitinase ABCI elution fractions. B—Silver stained. C—Coomassie Blue stained FIG. 3. Michaelis-Menten curves for cABCI and substrates.
Figure 2:
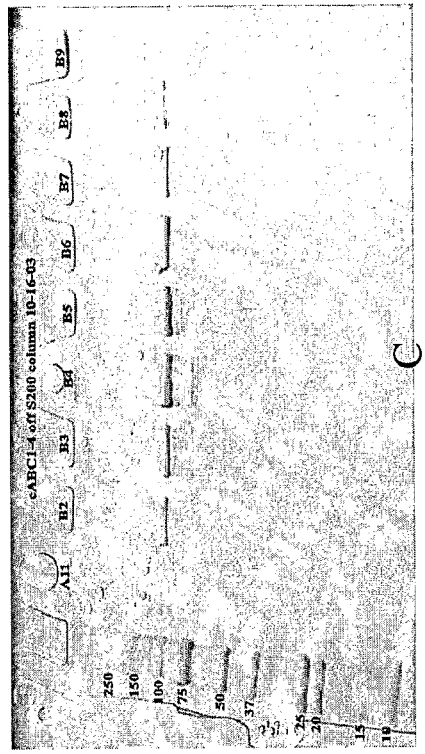
Figure 2:
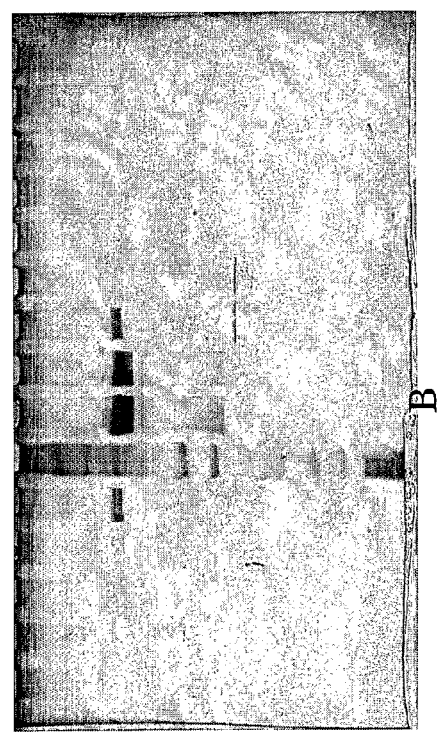

FIG. 2 depicts purification of chondroitinase ABCI by gel filtration. FIG. 2A is a chromatography profile for Sephacryl S300 26/60 column. FIG. 2B is an SDS-PAGE analysis of chondroitinase ABCI elution fraction from Sephacryl S300 26/60 column in 20 mM Tris, pH 8.0, 200 mM NaCl, 0.5% betaine. FIG. 2C is an SDS-PAGE analysis of chondroitinase ABCI elution fraction from Sephacryl S200 26/60 column in 20 mM NaAcetate, pH 5.5, 100 mM NaCl.

For lyophilization, the purified enzyme was dialyzed into volatile buffer of 0.1M $NH_4CO_3$, at about pH 8.0.

A gradient (4-20%) SDS-PAGE was performed, under reducing conditions, on the samples from the capture cation exchange column (start extract, flow-through, wash and SP elution pool) and gel filtration steps (S200 elution pool). The gel was stained with Coomassie blue. Gel analysis showed that the purification steps removed relatively all cell debris and contaminants, yielding a relatively pure enzyme sample.

Example 2

This example illustrates the enzyme activity of the purified recombinant chondroitinase ABCI of Example 1 as compared with the native enzyme. Chondroitinase ABCI enzymatic activity was assayed as described elsewhere herein. The recombinant chondroitinase ABCI of Example 1 of the present invention has the same or higher specific activity as the native enzyme, and much higher activity as the recombinantly expressed chondroitinase ABCI as shown below in Table 4.

TABLE 4

Enzyme Activity

| Enzyme Source | Specific Activity, U/mg |
|---|---|
| Native chondroitinase ABCI (Seikagaku) | 120 |
| Recombinant chondroitinase (Glyko) | 24 |
| Recombinant chondroitinase ABCI (Acorda) | 160 |

SEC characterization was performed on both the recombinant chondroitinase ABCI of Example 1 and native chondroitinase ABCI as described above. The elution profiles of recombinant chondroitinase ABCI and the native chondroitinase ABCI were the same. The recombinant chondroitinase ABCI of the present invention had a retention time and molecular weight expected for a chondroitinase ABCI.

Determination of isoelectric point for the recombinant chondroitinase ABCI. IEF-PAGE, as described elsewhere herein, was used to determine the pI value for the recombinant chondroitinase ABCI of Example 1. The recombinant protein of Example 1 exhibited 3 isomeric forms with a pI of about 7.8-8.0 for the major isoform. This value was higher than expected for a native enzyme.

Example 3

Chondroitinase ABCI, AC, and B were tested on a series of substrates and on rat spinal cord for specificity and activity using an improved anion exchange HPLC method. This method detects disaccharide CSPG cleavage products (Δdi-4DS and Δdi-6DS) with a quantification limit of 25 ng.

Measurements of the liberated disaccharide cleavage products revealed optimal enzyme concentrations, enzyme combinations, and substrate characteristics in rat spinal cord. The catalytic activity of chondroitinase ABCI and chondroitinase AC was synergistically enhanced with the addition of chondroitinase B. Ex vivo digestions of rat spinal cord yield Δdi-4DS and Δdi-6DS in the ratio of about 95:5. Time course studies revealed that maximum product formation occurred within 6 hours even though the enzymes are active for much longer. Product inhibition was ruled out as a cause for this observation.

Example 4

The following example illustrates the substrate specificity of the purified recombinant cABCI. cABCI (batch 7b) was reconstituted in 0.1 M sodium phosphate, and 50 mM NaCH$_3$COO at pH 7.4. Product formation rates were measured at different concentrations for chondroitins A, B, and C. The data were plotted and, where appropriate, fitted directly to the Michaelis-Menten equation for calculation of $K_m$ and $V_{max}$ values. The curves for chondroitin A, B and C exhibited saturation at high substrate concentrations that is typical for Michaelis-Menten kinetics. The following cABCI kinetic parameters were measured (FIGS. 1 and 3, Tables 3-5): $K_m$=0.033 mg/ml and $V_{max}$=283 U/mg for chondroitin A, $K_m$=0.021 mg/ml and $V_{max}$=74 U/mg for chondroitin B, $K_m$=0.025 mg/ml and $V_{max}$=188 U/mg for chondroitin C. Considering impurity levels that are present in each substrate (approximately 70%, for chondroitin A, approximately 85% for chondroitin B and approximately 90% for chondroitin C), cABCI seems to have similar affinity for all chondroitins, but it digests them at different specific rates (chondroitin A>chondroitin C>chondroitin B). Table 5 provides the raw data for Chondroitin A, B and C concentration dependence curves.

TABLE 5

Activity

| Substrate, mg/ml | Measured rates, nmole/min | Average activity, U/mg |
|---|---|---|
| Chondroitin A (70% purity) | | |
| 0.032 | 5.03; 5.54; 6.8 | 127.9 |
| 0.048 | 6.85; 7.39; 7.15 | 157.6 |
| 0.08 | 9.50; 8.25; 10.38 | 207.2 |
| 0.12 | 11.34; 9.78; 11.41 | 239.6 |
| 0.16 | 11.65; 12.24; 9.19 | 243.6 |
| 0.24 | 8.97; 14.65; 10.46; 12.44 | 257.0 |
| 0.32 | 10.95; 10.45; 10.98 | 238.4 |
| 0.48 | 11.81; 11.48; 11.34 | 255.1 |
| Chondroitin B (85% purity) | | |
| 0.04 | 9.85; 10.49 | 47.1 |
| 0.06 | 12.97; 10.67 | 54.7 |
| 0.08 | 12.46; 12.88 | 58.7 |
| 0.16 | 14.47; 14.50 | 67.0 |
| 0.20 | 14.58; 12.72 | 63.2 |
| 0.40 | 15.20; 15.31 | 70.6 |
| 0.60 | 15.21; 13.98; 16.03 | 69.8 |
| 0.80 | 16.10; 14.97 | 71.9 |
| Chondroitin C (90% purity) | | |
| 0.03 | 5.26; 3.91; 4.26 | 91.6 |
| 0.053 | 6.57; 6.41; 6.23 | 131.2 |
| 0.107 | 8.00; 8.55; 8.46 | 170.7 |
| 0.160 | 7.49; 7.98; 7.66 | 158.0 |
| 0.267 | 8.84; 8.49; 7.46 | 169.3 |
| 0.400 | 8.23; 9.23; 7.58 | 171.1 |
| 0.533 | 9.65; 8.33; 8.18 | 178.7 |

Figure 3:
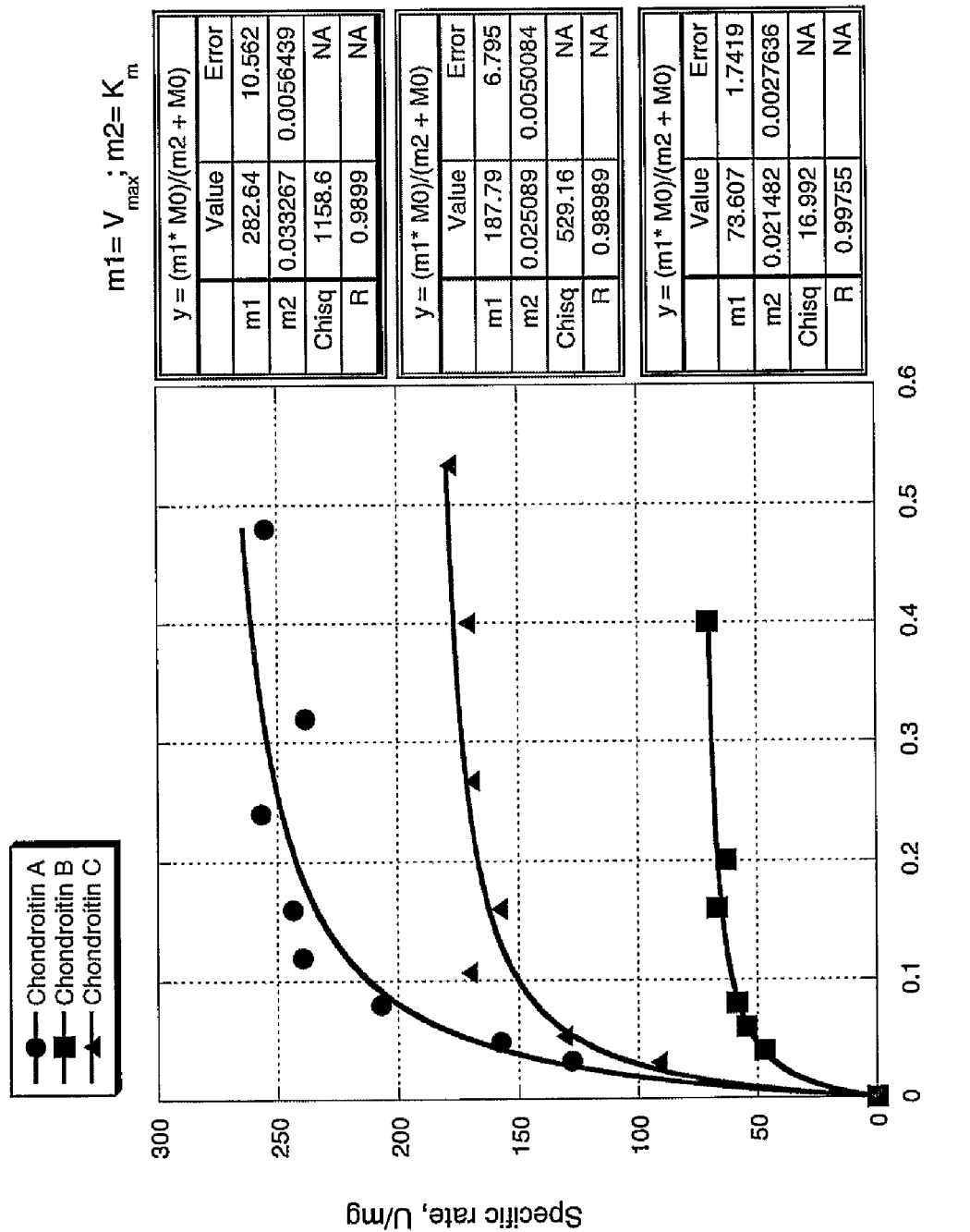
Figure 4A:
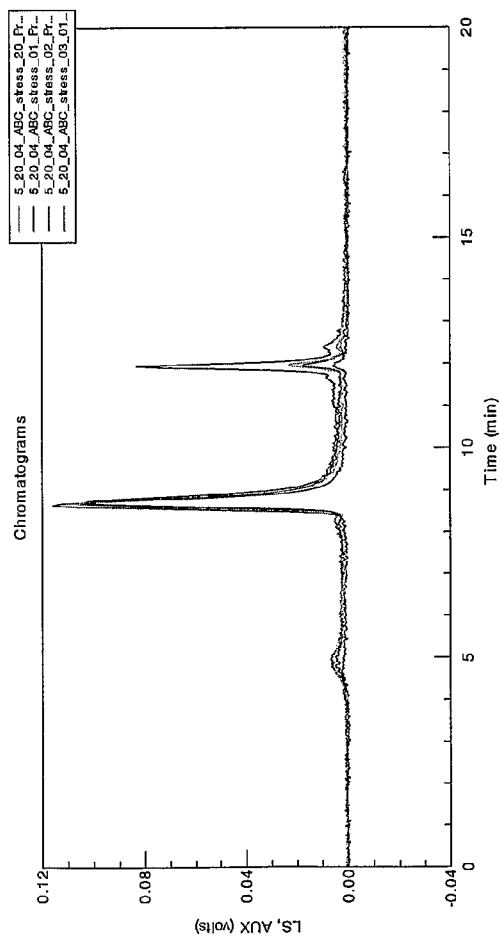
FIG. 4A-4E. The SEC light-scattering profiles of the cABCI non-treated (control) and stress-treated.
Figure 4B:
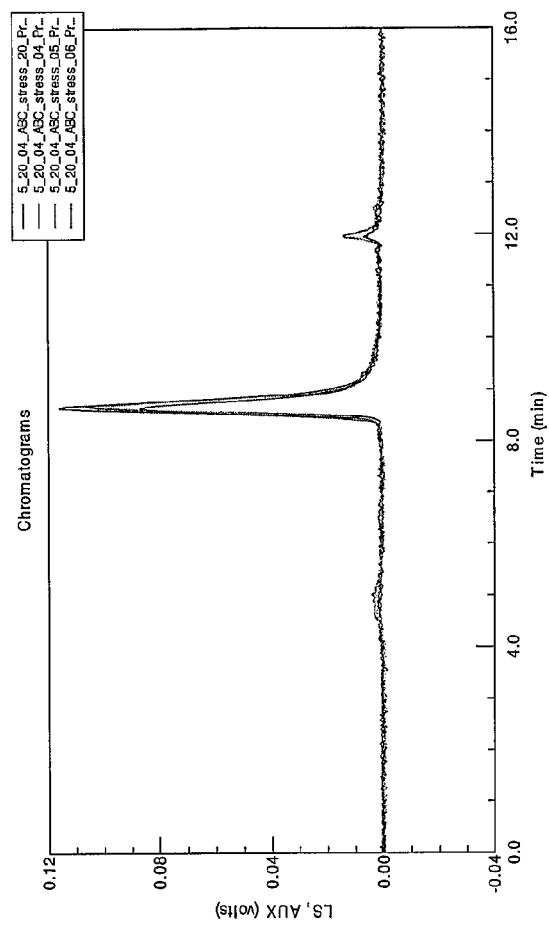
Figure 4C:
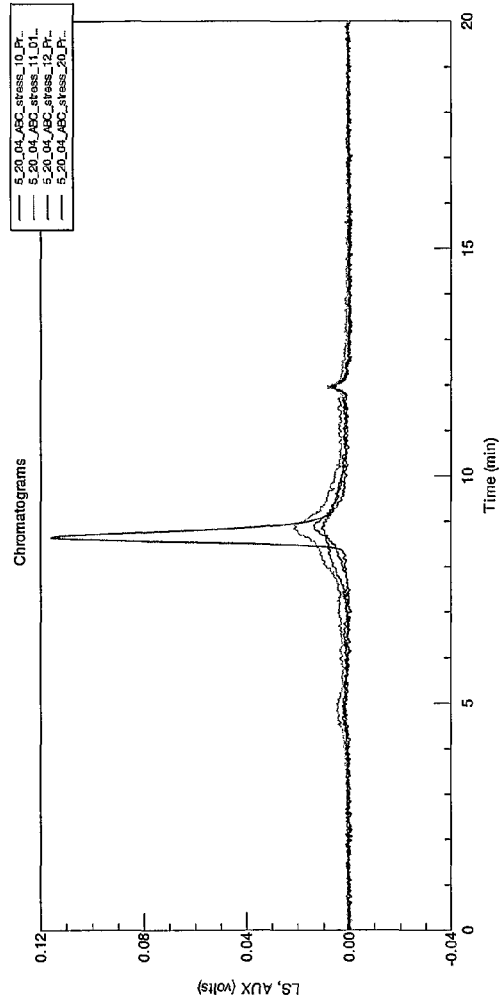
Figure 4D:
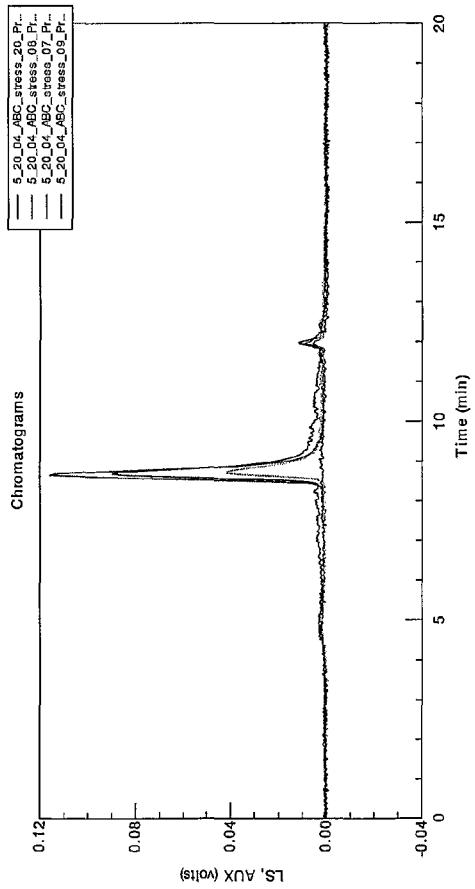
Figure 4E:
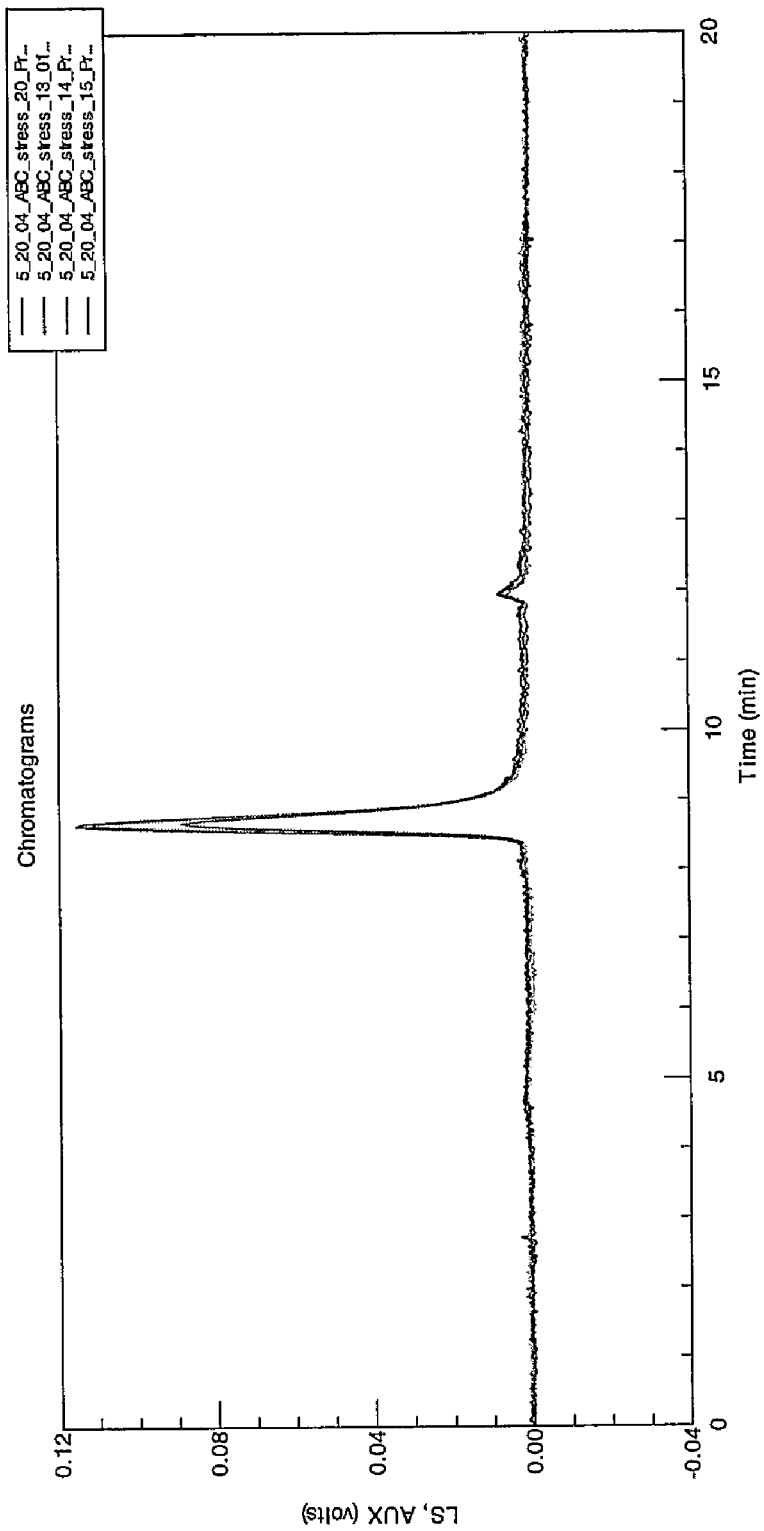

The average specific rates (U/mg) were plotted as a function of substrate concentration (mg/ml) and the data were directly fitted into the Michaelis-Menten equation for determination of cABCI kinetic parameters. FIG. 3 shows the Michaelis-Menten curves for cABCI and its substrates: chondroitin A, B and C.

Example 5

The inhibition of the purified chondroitinase ABCI enzyme in the presence of various divalent metal salts (1 mM) was measured. cABCI activity was assayed after metal additions were made. The inhibition capacity of the tested metals appears to be in the following order: Zn>>Ni>>Co>Ca>Mg. Notably, calcium and magnesium ions appear to have some measurable inhibitory effects on cABCI. Table 6 provides the metal inhibition of the recombinant cABCI.

TABLE 6

Metal Inhibition

| Metal salts, 1 mM | Measured rates, nmole/min | Retained activity, U/mg | % retained activity |
|---|---|---|---|
| None | 12.6; 13.9; 14.7 | 127 | 100 |
| CoCl$_2$ | 6.5; 6.6 | 61 | 48 |
| NiSO$_4$ | 1.8; 1.9 | 17 | 14 |
| ZnCl$_2$ | 0.23; 0.29 | 2.4 | 2 |
| CaCl$_2$ | 7.6; 9.2 | 78 | 61 |
| MgCl$_2$ | 9.1; 9.2 | 85 | 67 |
| FeCl$_2$ | interfered with an assay | ND | ND |
| Cu(CH$_3$COO)$_2$ | interfered with an assay | ND | ND |

Example 6

This example illustrates the effect storage buffer pH has on the stability of the purified recombinant cABCI. The lyophilized cABCI was reconstituted in 20 mM NaAcetate, pH 5.5, 100 mM NaCl buffer at 2.0 mg/ml concentration (using a BCA protein assay). Various pH conditions were achieved by diluting the reconstituted sample at about 1:2 ratios with 50 mM Bis-Tris propane buffers with various pH conditions. The cABCI concentration of the final samples was about 1 mg/ml. The samples were stored at about 4° C. and their activity was measured at 24 hrs, 48 hrs and 72 hrs. Table 7 provides the measured activity data for the recombinant cABCI samples stored under different pH conditions.

TABLE 7

Measured Activities

| Storage pH | Starting rates, nmol/min | Rates after 24 hrs at 4° C., nmole/min | Rates after 48 hrs at 4° C., nmole/min | Rates after 72 hrs at 4° C., nmole/min | Average rates, nmole/min |
|---|---|---|---|---|---|
| 4 | 1.63; 2.47 | 5.47; 5.28 | 5.16; 5.00 | 4.84; 5.59 | 4.4 |
| 5 | 2.55; 3.13 | 5.92; 4.09 | 4.00; 3.70 | 4.89; 4.59 | 4.1 |
| 6 | 3.93; 4.04 | 4.46; 3.74 | 2.64; 2.78 | 4.90; 4.67 | 3.9 |
| 7 | 4.15; 5.55 | 4.41, 4.57 | 4.97, 5.09 | 4.91, 4.51 | 4.8 |
| 8 | 4.43, 3.49 | 3.62, 4.21 | 4.29, 4.04 | 4.24, 4.80 | 4.1 |
| 9 | 4.47, 3.65 | 4.53, 4.27 | 5.09, 4.49 | 5.05, 4.10 | 4.5 |

No significant differences were observed between the samples stored at different pH conditions. pH 7.4 is preferred in order to be within the physiological pH range.

Example 7

The recombinant cABCI was subjected to different stress conditions. The activity and protein concentration data for the recombinant cABCI samples after various stress treatments are presented in Table 8.

TABLE 8

Activity Following Stress Conditions

| Sample# | Treatment | Treatment points | Concentration, mg/ml | Measured rates, nmole/min | Activity, U/mg |
|---|---|---|---|---|---|
| Control | 4° C. | | 0.976 | 31.7; 30.0 | 126.4 |
| 1 | Freezing | 1 cycle | 0.952 | 30.1; 29.2 | 124.6 |
| 2 | Freezing | 2 cycle | 0.952 | 22.8; 27.8 | 108.6 |
| 3 | Freezing | 3 cycle | 0.932 | 27.3; 25.8 | 114 |
| 4 | $H_2O_2$ | 0.5 mM | 0.952 | 24.3; 22.7 | 98.8 |
| 5 | $H_2O_2$ | 5 mM | 0.964 | 4.3; 6.1 | 21.3 |
| 6 | $H_2O_2$ | 20 mM | 0.982 | 1.1; 1.4 | 5.15 |
| 7 | Vortex | 5 min | 0.765 | 18.4; 17.9 | 94.8 |
| 8 | Vortex | 20 min | 0.432 | 13.0; 12.3 | 117 |
| 9 | Vortex | 60 min | 0.066 | 0.7; 0.8 | 46 |
| 10 | UV | 40 min | 0.976 | 0.1; 0.3 | 0.8 |
| 11 | UV | 1 hr | 0.976 | 0.1; 0.1 | 0.36 |
| 12 | UV | 2 hrs | 0.976 | 0.1; 0.1 | 0.33 |
| 13 | 37° C. | 1 hr | 0.922 | 18.9; 16.0 | 75.5 |
| 14 | 37° C. | 4 hrs | 0.934 | 15.8; 17.0 | 70.1 |
| 15 | 37° C. | 20 hrs | 0.801 | 14.6; 8.8 | 58.3 |

The stress-treated samples were also analyzed by SEC with a light-scattering detector. The SEC light-scattering profiles of the cABCI non-treated (control) and stress-treated samples are shown in FIGS. 4A-4E.

The recombinant cABCI, at about 1 mg/ml, did not appear to be affected by 3 cycles of freezing and thawing. The enzyme was precipitated and inactivated in a time-dependent manner when vortexing was used as the stressor. Hydrogen peroxide exposure resulted in loss of activity in a concentration-dependent manner with the noticeable changes in its isoform profiles on IEF-PAGE. Exposure to UV light had a negative effect on the activity of cABCI. The enzyme did not appear to be stable at 37° C. and its loss of activity appeared to be time dependent. Thermally inactivated samples had a decrease in protein concentration and showed changes in the isoform profile similar, but in lesser degree, to the ones observed for hydrogen peroxide treated samples.

A weak cation exchange (CEX) HPLC method was developed in order to quantify cABCI oxidation products. Therefore, another stress study was conducted in order to identify and correlate the presence of oxidation products with the loss of enzymatic activity. Some stress treatments were repeated under milder conditions than the ones used in the previous study (UV exposure). The reconstituted cABCI samples (0.6 mg/ml) were exposed to 2 different sources of UV light (long-distance and short-distance exposure) for about 0.5, 1, 3 and 5 minutes and thermal inactivation (about 37° C.) in 20 mM NaAcetate, pH 5.5, 100 mM NaCl buffer. The samples were assayed for activity and by IEF-PAGE, SDS-PAGE, oxyblot and CEX-HPLC. The results are described below.

Following oxidation treatment, an additional peak emerged on CEX-HPLC and is presumed to be the oxidized chondroitinase in FIG. 5. This peak increased with an increase in the UV exposure time. The total areas under the curve in the RP-HPLC chromatograms remained nearly the same.

Figure 5A:
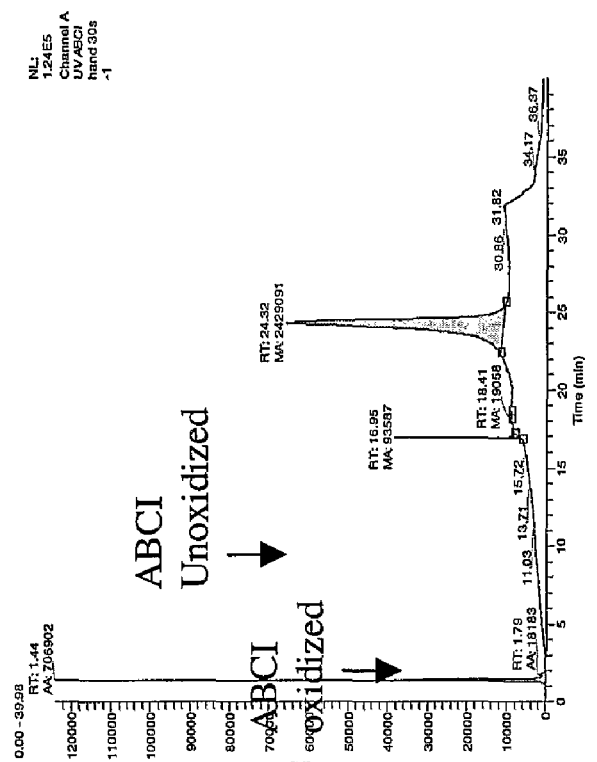
FIG. 5. Weak cation-exchange HPLC analysis of the UV-treated cABCI samples. 5A. Initial sample; 5B. after 30 seconds UV exposure; 5C. after 2 minutes UV exposure; 5D. after 5 minutes UV exposure.
Figure 5B:
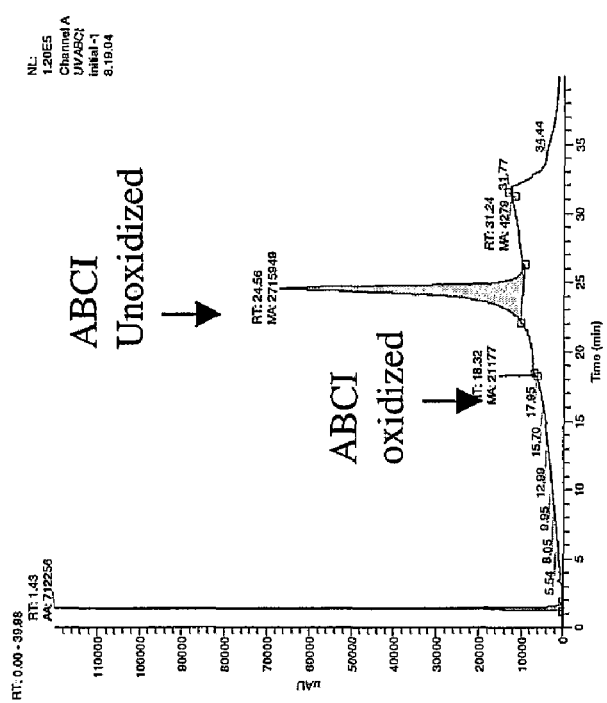
Figures 5C, 5D:

FIG. 5 shows a weak CEX-HPLC analysis of the UV-treated cABCI samples. Shown are chromatograms of cABCI before (FIG. 5A) and following 0.5 (FIG. 5B), 3 (FIG. 5C) and 5 minutes (FIG. 5D) of close UV (hand-held light source) exposure.

Table 9 provides the cABCI activity data for non-treated (control) and stress-treated samples.

TABLE 9

Activity for Stress Treated and Control Samples.

| Samples | Rates, nmole/min, | Activity, U/mg, |
|---|---|---|
| Control | 49.3; 40.9; 40.9 | 146.7 |
| UV light long-distance | | |
| 0.5 min | 53.5; 37.9; 46.3 46.304 45.87 | 154.0 |
| 1 min | 34.0; 44.6; 44.0 | 137.1 |
| 3 min | 37.62; 39.3; 32.4 | 122.2 |
| 5 min | 20.4; 29.2; 23.9 | 82.04 |
| UV light short-distance | | |
| 0.5 min | 41.0; 36.0; 35.2 | 125.5 |
| 1 min | 16.3; 19.8; 19.2 | 61.9 |
| 3 min | 8.6; 9.3; 7.8 | 28.7 |
| 5 min | | |
| 1 day at 37° C. | 13.3; 18.0; 14.1 | 50.9 |

Following exposure to UV and heat, cABCI samples were assayed for activity by the previously described spectrophotometric assay. There appears to be a correlation between the relative decrease in area of unoxidized cABCI peak with the relative decrease in activity (U/mg). Table 10, shown below, is the correlation of the decrease in the non-oxidized cABCI with the activity after exposure to short-distance and long-distance UV light.

TABLE 10

Activity After UV Exposure

| Time, Mins | Peak Area | Control Peak Area | % of Initial Area | % of Initial Activity |
|---|---|---|---|---|
| 0 | 19239 | 2739978 | 100.0 | 100.0 |
| UV light short-distance | | | | |
| 0.5 | 93587 | 2429091 | 88.7 | 85.6 |
| 1 | 171634 | 1225441 | 44.7 | 42.1 |
| 3 | 180745 | 292674 | 10.7 | 19.7 |
| 5 | 181961 | 216126 | 7.9 | 6.4 |
| UV light long distance | | | | |
| 0.5 | 31900 | 2770293 | 101.1 | 105.0 |
| 1.0 | 28732 | 2670994 | 97.5 | 93.6 |
| 3.0 | 68466 | 2410100 | 88.0 | 83.3 |
| 5.0 | 89149 | 1877997 | 68.5 | 55.8 |

Figure 6:
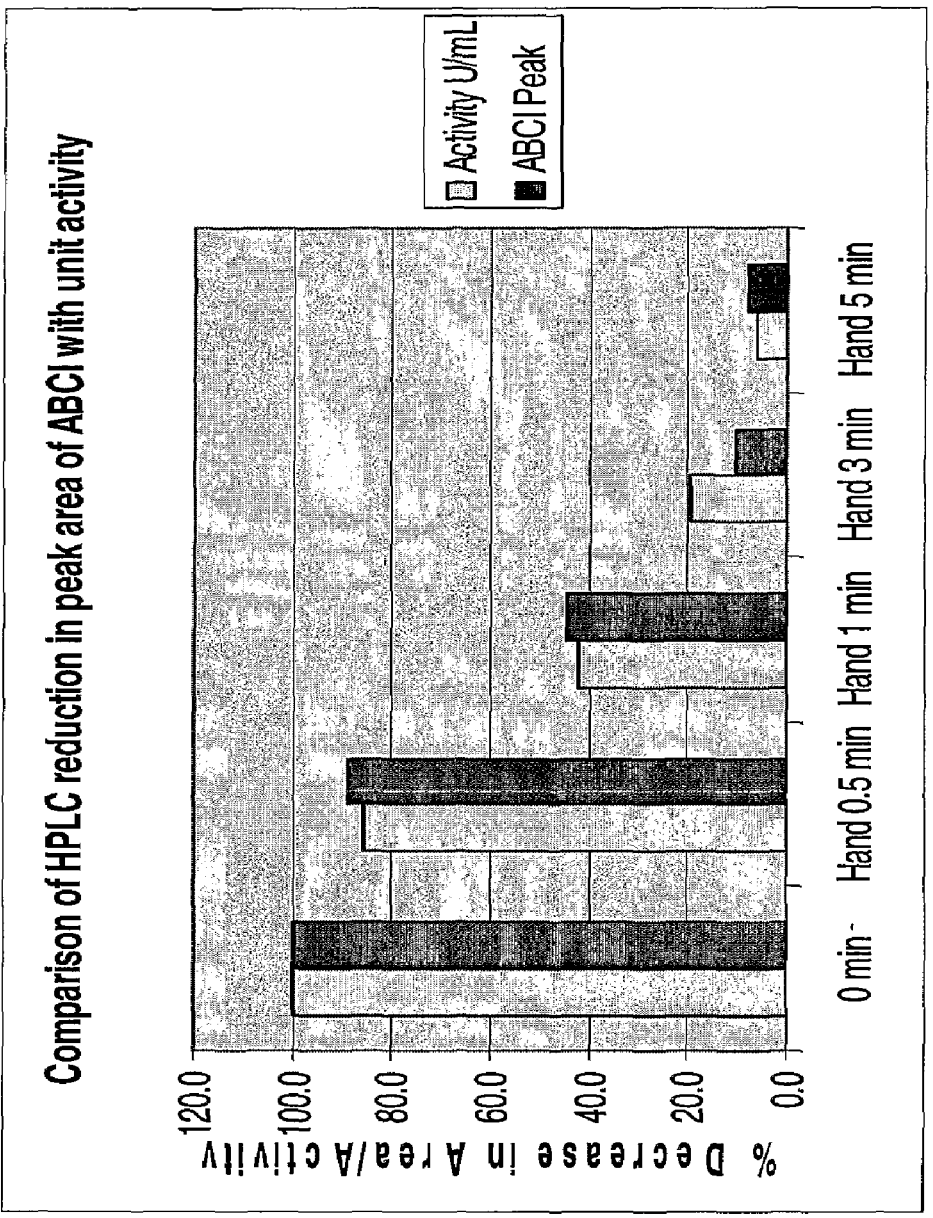
FIG. 6. Comparison of HPLC peak area of ABCI with unit activity.
Figure 7:
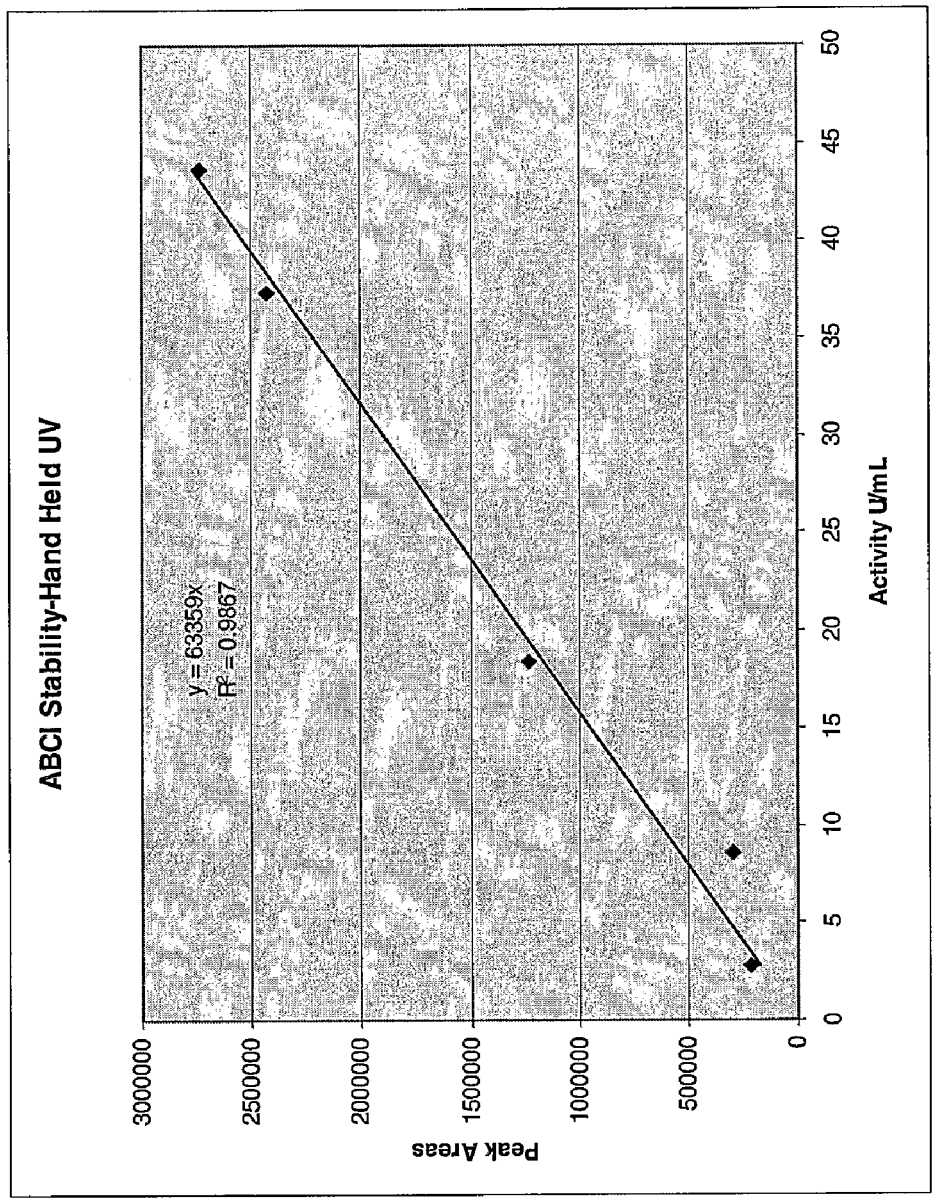
FIG. 7. ABCI stability-hand held UV.
Figure 8:
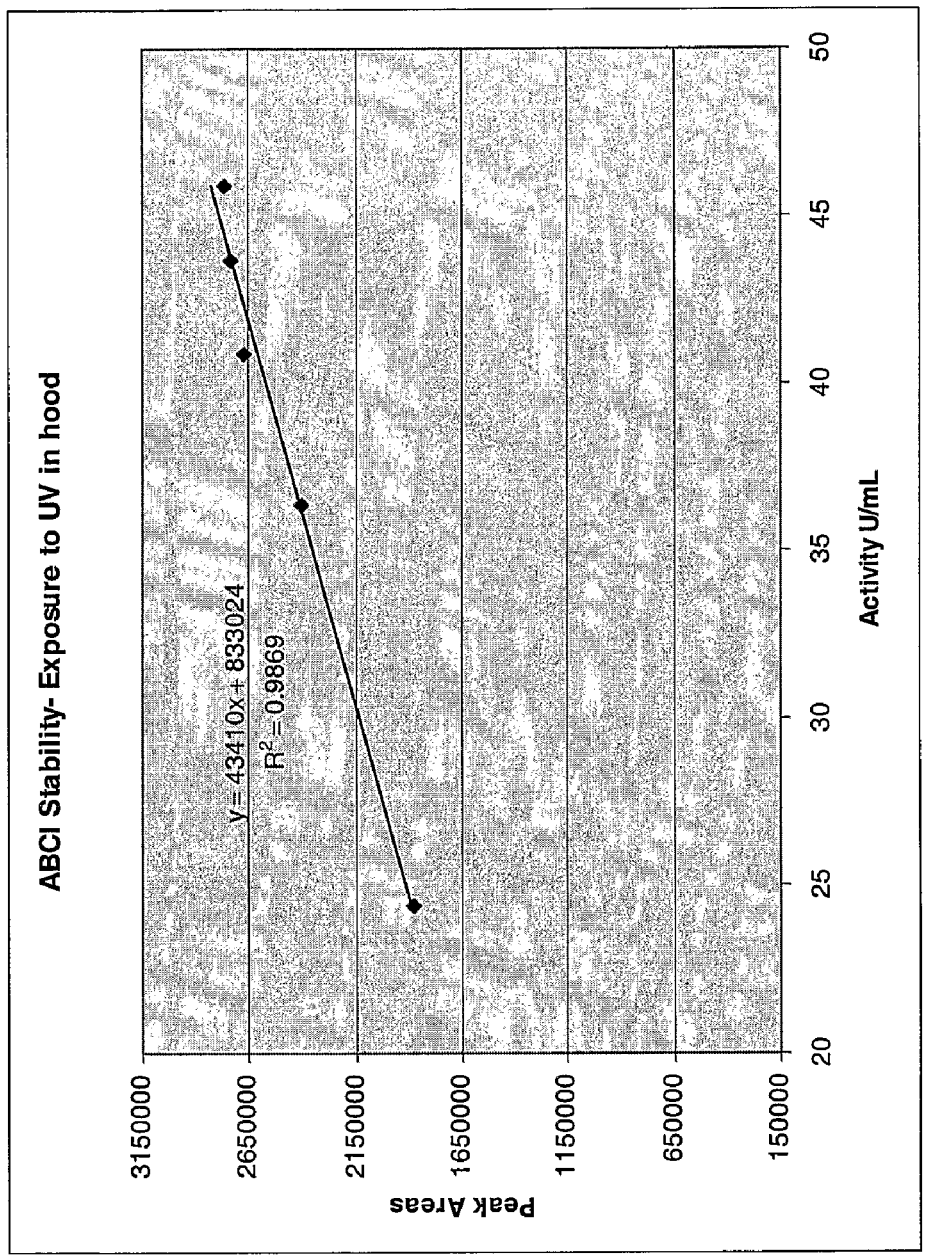
FIG. 8. ABCI stability-exposure to UV in hood.
Figure 9B:
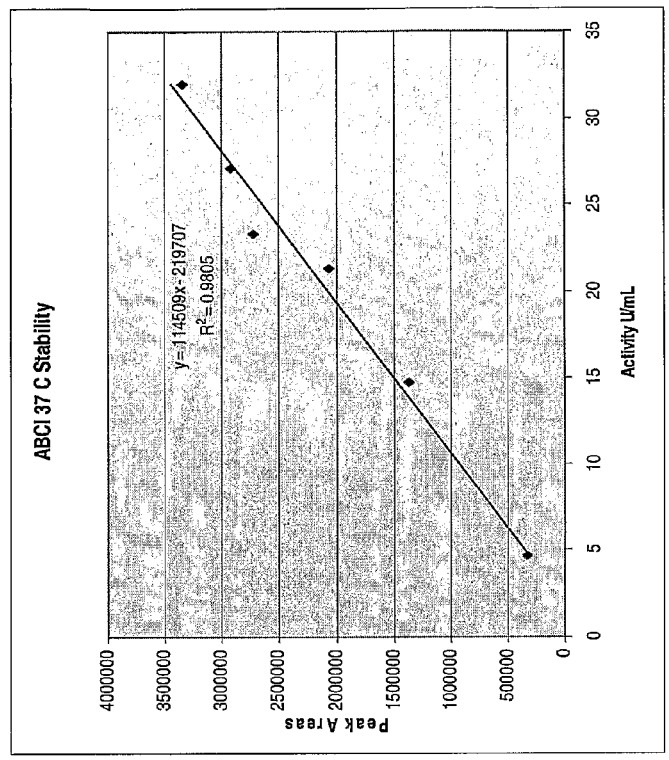
FIG. 9. Correlation of cABCI activity data with HPLC profile of cABCI during thermal inactivation. 9A. Histogram of the percent of initial peak areas on HPLC and the percent of initial activity by spectrophotometric assay. 9B. Regression of peak areas and activities by spectrophotometry.
Figure 9A:
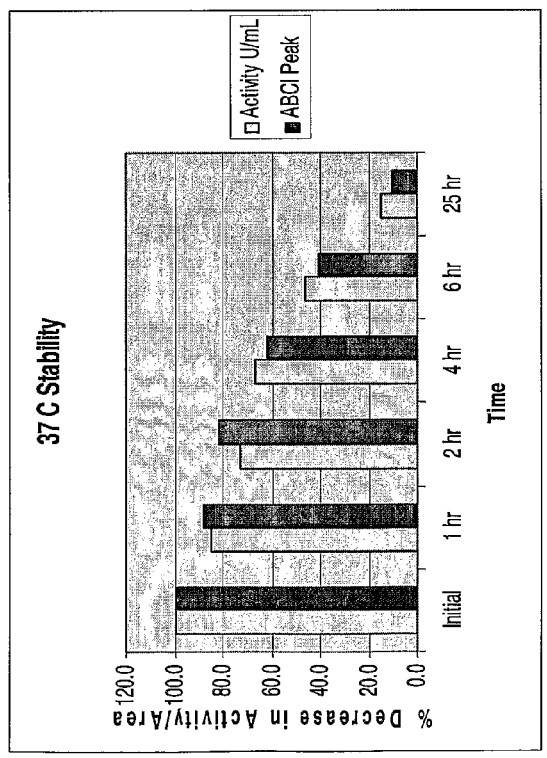

FIGS. 6-8 show the correlation of the presence of the cABCI oxidized product with reduction in enzyme activity. Some correlation between the appearance of the oxidized product and the enzymatic activity was also observed for thermally inactivated samples. cABCI samples were exposed to heat and assayed for activity by spectrophotometry and for oxidized product by CEX-HPLC as described above.

Table 11 shows data of cABCI activity measurements after incubation at 37° C. for 0 to 24 hours. One vial of cABCI Batch 7b was reconstituted in 50 mM sodium acetate/100 mM sodium chloride. Samples were incubated at 37° C. for 1, 2, 4, 6 & 24 hrs. The concentration of the control sample (prior to any incubations) was determined. The sample's A280 was 0.88, and the concentration was calculated to be equal to about 0.53 mg/mL.

TABLE 11

Activity After Incubation

| Samples | Measured rates, nmole/min | **Activity, U/mg |
|---|---|---|
| Control, 4° C.* | 34.4; 26.7 | 181.85 |
| 1 hr | 26.6; 27.5 | 161.17 |
| 2 hr | 22.0; 26.7; 21.3 | 138.87 |
| 4 hr | 21.0; 21.5 | 126.56 |
| 6 hr | 19.9; 11.6; 17.9; 9.6 | 87.79 |
| 24 hr | 4.7; 4.7 | 27.91 |

Table 12. Correlation of cABCI activity data with HPLC profile of cABCI during thermal inactivation.

TABLE 12

Activity After Thermal Inactivation

| Time | Peak Area | Control Peak Area | % of Initial Area | % of Initial Activity |
|---|---|---|---|---|
| Initial | 49607 | 3342595 | 100 | 100.0 |
| 1 hr | 60633 | 2926126 | 87.5 | 84.7 |
| 2 hr | 77000 | 2728818 | 81.6 | 72.8 |
| 4 hr | 88621 | 2068080 | 61.9 | 66.6 |
| 6 hr | 134161 | 1375960 | 41.2 | 45.9 |
| 25 hr | 311574 | 336266 | 10.1 | 14.7 |

Following activity determination and weak CEX-HPLC analysis, the thermally and UV-inactivated samples were also analyzed by SDS-PAGE, IEF-PAGE and Oxyblot.

The incubation at 37° C. study was repeated for additional buffer conditions: 0.1M NaPhosphate, pH 7.4, 50 mM NaAcetate and 0.75M NaPhosphate, 50 mM NaAcetate, as described in Example 8.

Example 8

In the following study, different buffers were used to determine enzyme stability. Recombinant cABCI was reconstituted in 50 mM NaAcetate, pH 6.5, 100 mM NaCl and diluted 1:3 with 0.2M solutions of the sodium acetate, sodium phosphate, Tris and HEPES. Following an overnight incubation at 37° C. in the different buffers the activity of cABCI was determined. The data are presented in Table 13.

TABLE 13

Activity based on Buffer System

| Buffer system | Measured Rates, nmole/min | Activity, U/mg |
|---|---|---|
| Acetate, pH 6.5 after 4° C. incubation | 31.7; 30.0 | 126.4 |
| Acetate, pH 6.5 after 37° C. incubation | 16.4; 20.8 | 82.4 |
| Tris, pH 8.1 after 37° C. incubation | 15.5; 18.9 | 76.1 |
| NaPhosphate, pH 7.4 after 37° C. incubation | 28.4; 28.0 | 124.8 |
| HEPES, pH 6.8 after 37° C. incubation | 24.2; 26.9 | 113 |

This study revealed that the phosphate buffer provided the most protection for cABCI against thermal inactivation.

Example 9

This example demonstrates the effect of various protein stabilizers (buffers) and excipients on their ability to stabilize the cABCI. The results of this evaluation of different protein stabilizers and buffer conditions for cABCI buffer formulation are listed in Table 14.

TABLE 14

Activity based on Protein Stabilizers and Buffers

| Treatment | Starting Rates, nmole/min | Starting Activity, U/mg | Rates 72 hrs, 37° C., nmole/min | Activity 72 hrs, 37° C., U/mg | % Activity Retained |
|---|---|---|---|---|---|
| Control: 100 mM NaPhosphate pH 7.4, 50 mM NaAcetate, 50 mM NaCl | 8.6; 9.8 | 91.6 | 2.6; 2.4 | 5.3 | 5.8 |
| 500 mM NaCl | 7.9; 10.0 | 89.5 | 14.2; 12.3 | 17.7 | 19.7 |
| 750 mM NaPhosphate | 11.3; 12.2 | 117.9 | 11.3; 11.8 | 106.0 | 90.0 |
| 0.1 mM Hydroquinone | 10.3; 10.2 | 102.9 | 0.03; 0.09 | 0 | 0 |
| 1% Mannitol | 11.6; 9.2 | 104.5 | 4.6; 6.1 | 7.6 | 7.2 |
| 0.3M Sucrose | 10.5; 8.9 | 87.3 | 13.0; 13.7 | 13.3 | 15.3 |
| 10% Glycerol | 9.6, 10.2 | 98.8 | 3.6; 3.1 | 3.5 | 3.6 |
| 100 mM Arginine | 10.2; 11.6 | 109.2 | 0.06; 0.12 | 2.5 | 2.3 |
| 0.3M Trehalose | 8.7; 8.7 | 87.1 | 0.8; 0.8 | 1.2 | 1.4 |
| 50 mM NaPhosphate | 3.0; 3.0 | 51.4 | 0.2; 0.3 | 3.3 | 6.4 |
| 50 mM NaPhosphate 0.01% Polyethylimid | 4.5; 4.3 | 68.3 | 2.2; 3.0 | 11.3 | 16.5 |

* shown are examples from two trials

Table 15 provides an evaluation of EDTA as additive to cABCI buffer formulation.

TABLE 15

Activity following EDTA Administration

| Treatment | Starting rates, nmole/min | Starting Activity, U/mg | Rates 36 hrs, 37° C., nmole/min | Activity 36 hrs, 37° C., U/mg | % Activity Retained |
|---|---|---|---|---|---|
| 50 mM NaPhosphate | 5.9; 6.1 | 83.3 | 23.9; 26.0 | 53.1 | 63.7 |
| 50 mM NaPhosphate 1 mM EDTA | 6.0; 4.8 | 75.0 | 18.0; 21.1 | 65.2 | 86.9 |
| 750 mM NaPhosphate | 12.0; 10.8 | 158.2 | 5.9; 6.2 | 151.1 | 95.5 |
| 750 mM NaPhosphate 1 mM EDTA | 11.3; 8.2 | 135.8 | 5.9; 6.0 | 149.5 | 110.1 |

None of the excipients or buffers, except sodium phosphate at 750 mM, was effective against cABCI thermal inactivation. 500 mM NaCl also showed some improvement in cABCI thermal stability. The results suggested that ionic strength might play a role in protection of cABCI from thermal inactivation.

Example 10

This example demonstrates the effects different salts and different salt concentrations have on the stability of cABCI using sodium chloride in the cABCI formulation buffer. Recombinant cABC was reconstituted in 50 mM Na Phosphate pH 7.4 at approximately 2 mg/ml. An initial activity reading was taken to determine the base level of activity. Chondroitinase (1 mg/ml) was diluted into sodium chloride (NaCl) in 50 mM Na Phosphate, pH 7.4 at concentrations ranging from 0 to 1M. The samples were allowed to incubate at 37° C. for 48 hours. After two days the samples were assayed for activity. The data are presented below in Table 16-18 and FIGS. 10 and 11. Table 16 shows that thermal stability of cABCI is dependent on the on ionic strength of the NaCl in the presence of 50 mM Na Phosphate buffer.

TABLE 16

Thermal Stability and Ionic Strength

| NaCl, mM | Measured Rates, nmole/min | Activity 48 hrs, 37° C., U/mg | Retained Activity, % |
|---|---|---|---|
| 0 | 0.33; 0.33 | 3.3 | 5.1 |
| 10 | 0.11; 0.27 | 2.0 | 3.0 |
| 100 | 0.79; 0.92 | 8.5 | 13.2 |
| 250 | 0.83; 0.84 | 8.4 | 12.9 |
| 500 | 1.30; 1.76 | 15.3 | 23.7 |
| 1000 | 1.80; 1.67 | 17.4 | 26.9 |

Figure 10:
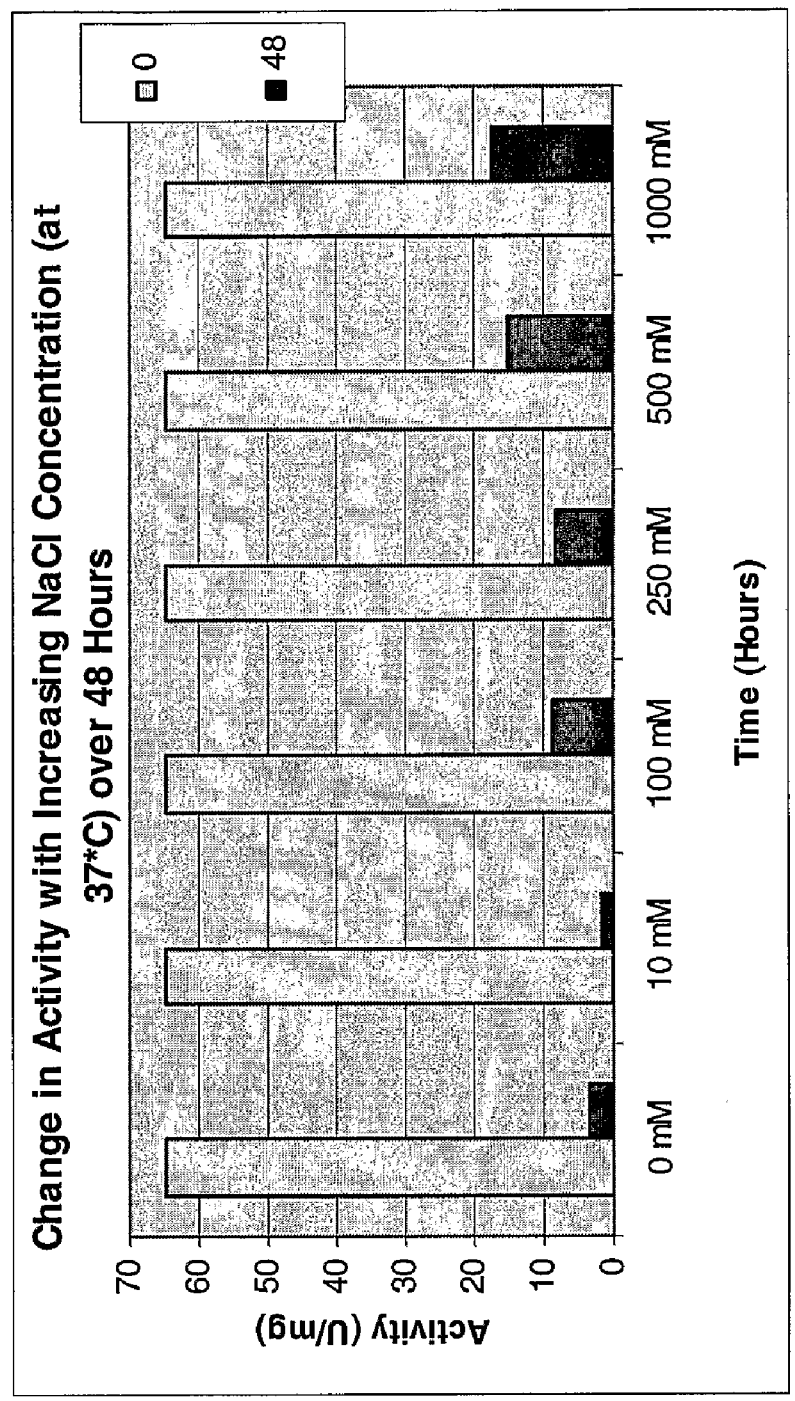
FIG. 10. Dependence of cABCI thermal stability on ionic strength of in the presence of 50 mM Na Phosphate buffer.
Figure 11:
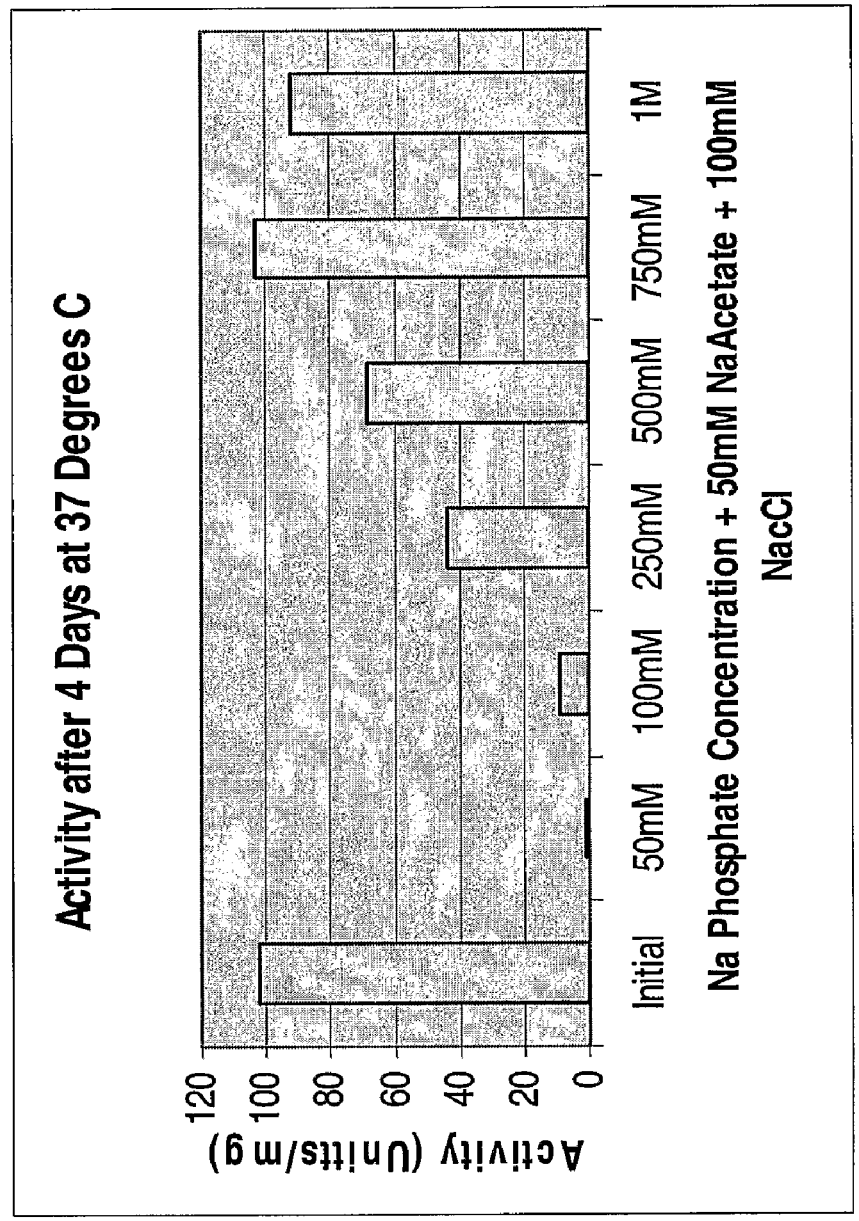
FIG. 11. Dependence of cABCI thermal stability on concentration of buffer species in the presence of 100 mM NaCl and 50 mM NaAcetate.

FIG. 10 is a graphic representation of the data shown in Table 16. Table 17 shows the effects of buffer concentration on the thermal stability of cABCI is dependent on the on the concentration of the buffer in the presence of 100 mM NaCl and 50 mM NaAcetate.

TABLE 17

Thermal Stability and Buffer

| Phosphate buffer, mM | Rates, nmole/min | Activity 96 hrs, 37° C., U/mg | % Retained Activity |
|---|---|---|---|
| 50 | 0.10; 0.07 | 0.83 | 0.8 |
| 100 | 4.4; 4.6 | 9.0 | 8.8 |
| 250 | 18.6; 20.8 | 43.9 | 43.0 |
| 500 | 16.4; 15.3 | 69 | 67.6 |
| 750 | 24.6; 20.8 | 103.3 | 101.4 |
| 1000 | 16.9; 19.9 | 92.2 | 90.5 |

Figure 12:
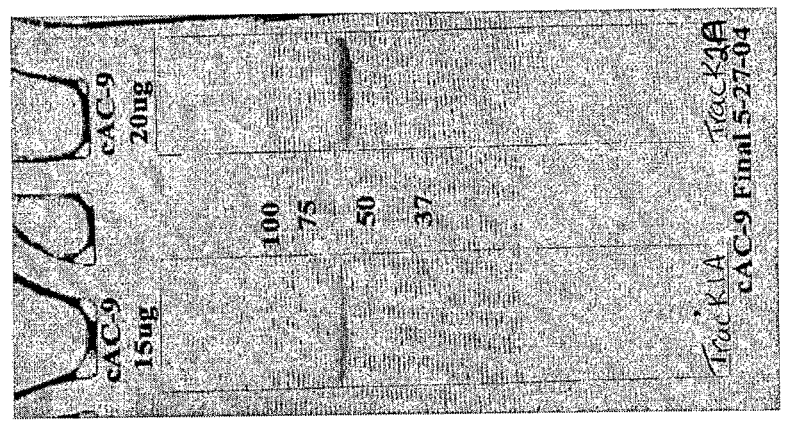
FIG. 12. SDS-PAGE analysis of the final purified chondroitinase AC.

FIG. 12 is a graphic representation of the data presented in Table 17. The data showed that the increase in ionic strength appears to improve the cABCI thermal stability. 750 mM Na Phosphate also provides protection for cABCI.

The next set of experiments was performed in order to optimize the ionic strength conditions while maintaining the lowest possible salt concentration in the final formulation. The thermal stability of cABCI was determined in a solution of sodium phosphate and sodium sulfate. Sodium sulfate is known for its protein stabilizing effects. The concentrations of both salts were varied and the catalytic rates of cABCI were measured following incubations at 37° C. for 19 hrs, 48 hrs, 120 hrs, and 192 hrs.

Table 18 depicts optimization of the sodium phosphate and the sodium sulfate concentrations for the cABCI buffer formulation. The cABCI was reconstituted in 0.1M $Na_2HPO_4$, 50 mM NaAcetate, pH 7.4. All samples had cABCI concentrations of 0.37 mg/ml, and the same acetate concentration (50 mM), same pH (7.4) but different phosphate and sulfate concentrations. The samples were maintained in a 37° C. water bath for the indicated times (19 hrs, 48 hrs, 120 hrs, and 192 hrs).

TABLE 18

Formulations of Sodium Phosphate and Sodium Sulfate

| Sample | Rate after 19 hrs, nmole/min (Activity, U/mg) | Rates after 48 hrs, nmole/min (Activity, U/mg) | Rate after 120 hrs, nmole/min (Activity, U/mg) | Rate after 192 hrs, nmole/min (Activity, U/mg) |
|---|---|---|---|---|
| Control, 4° C. 0.37 mg/ml | 33.701 35.646 40.353 (197.66) | N/A | N/A | N/A |
| 0.05 M $Na_2HPO_4$ | | | | |
| #1 | 0.185 0.2766 (1.25) | N/A | N/A | N/A |
| #2 0.15M $Na_2SO_4$ | 0.984 0.777 (4.8) | N/A | N/A | N/A |
| #3 0.22M $Na_2SO_4$ | 1.3588 1.3924 (7.44) | N/A | N/A | N/A |
| #4 0.3M $Na_2SO_4$ | 1.9721 1.8339 (10.29) | N/A | N/A | N/A |
| 0.1M $Na_2HPO_4$ | | | | |
| #5 | 1.1044 0.9543 (5.56) | N/A | N/A | N/A |
| #6 0.15M $Na_2SO_4$ | 1.6853 1.4162 (8.38) | N/A | N/A | N/A |
| #7 0.22M $Na_2SO_4$ | 2.7917 2.5572 (14.46) | N/A | N/A | N/A |
| #8 0.3M $Na_2SO_4$ | 3.3989 3.8001 (19.46) | N/A | N/A | N/A |
| 0.1M $Na_2HPO_4$ | | N/A | N/A | N/A |
| #9 | 3.9975 3.2614 (19.62) | N/A | N/A | N/A |
| #10 0.15M $Na_2SO_4$ | 7.7154 5.48 (35.66) | N/A | N/A | N/A |
| #11 0.22M $Na_2SO_4$ | 5.1651 4.9371 (27.3) | N/A | N/A | N/A |
| #12 0.3M $Na_2SO_4$ | 8.4036 8.6568 (46.1) | 2.64 3.24 (15.89) | 0.06 0.23 0.1 0.02 (0.27) precip | N/A |
| 0.4M $Na_2HPO_4$ | | | | |
| #13 | 11.995 14.978 (72.9) | 8.08 9.74 9.97 (50.07) | 1.15 1.05 1.41 (0.45) precip | N/A |
| #14 0.15M $Na_2SO_4$ | 20.921 17.78 (104.6) | 17.2 15.5 (88.38) | 5.29 5.25 (14.2) precip | N/A |
| #15 0.22M $Na_2SO_4$ | 20.066 22.769 (115.77) | 14.5 19.0 15.26 11.72 (81.7) | 7.48 9.75 (23.3) precip | N/A |
| #16 0.3M $Na_2SO_4$ | 18.07 16.462 (93.32) | 16.4 18.1 12.8 19.0 (90.0) | 13.4 12.4 8.2 (30.5) precip | N/A |
| 0.75M $Na_2HPO_4$ | | | | |
| #17 cABCI | 30.481 27.388 28.128 (154.95) | 22.3 28.7 30.9 26.1 (145.9) | 20.3 7.0 9.1 13.8 (90.45) precip | 13.234 13.749 (73) |

The data for 19 hrs samples are summarized in Table 19 as percent activity remaining.

TABLE 19

Percent Activity After 19 Hours

| | $Na_2HPO_4$ | | | | |
|---|---|---|---|---|---|
| $Na_2SO_4$ | 0.05M | 0.1M | 0.2M | 0.4M | 0.75M |
| 0 | 0.6 | 2.8 | 9.9 | 37.0 | 78.7 |
| 0.15M | 2.4 | 4.3 | 18.1 | 53.1 | NA |
| 0.22M | 3.8 | 7.4 | 13.9 | 58.8 | NA |
| 0.3M | 5.2 | 9.9 | 23.4 | 47.4 | NA |

Although sodium sulfate appears to improve the cABCI stability, the protection from phosphate appears to be more pronounced. 0.75M sodium phosphate buffer was selected for cABCI formulations for use at 37° C. This buffer was not selected for formulations that may be stored at lower temperatures due to its propensity to precipitate.

Example 11

This example illustrates the effect of enzyme concentration on its thermal stability. Samples were suspended in 0.75 M phosphate pH 7.4, 50 mM Na Acetate. To determine the working range of cABCI concentrations, cABCI thermal stability at different enzyme concentrations was measured. It was observed that cABCI at low concentrations were as stable as cABCI at high concentrations (see Table 20). Also it was found that cABCI at high concentrations tends to precipitate after prolong exposure to 37° C. To avoid this problem, for example, cABCI concentrations may be kept below ~0.4 mg/ml as shown in Table 20.

TABLE 20

37° C. stability of cABCI samples at different enzyme concentrations in 0.75M NaPhosphate buffer.

| cABCI, mg/ml | Starting Rates, nmole/min (Activity, U/mg) | 19 hrs at 37° C. Rates, nmole/min (Activity, U/mg) | 48 hrs at 37° C. Rates, nmole/min (Activity, U/mg) | 120 hrs at 37° C. Rates, nmole/min (Activity, U/mg) | 192 hrs at 37° C. Rates, nmole/min (Activity, U/mg) |
|---|---|---|---|---|---|
| 0.75 | NA | 26.3; 16.1; 21.9 (115.9) | 21.8; 19.6; 27.1 (101.5) | precipitate | 2.7; 2.5 (14) |
| 0.35 | 33.7; 35.6; 40.3 (197.66) | 30.5; 27.3; 28.1 (155.0) | 22.3; 28.7; 30.9; (145.9) | precipitate | 13.2; 13.7 (73) |
| 0.18 | NA | 24.3; 24.3; 26.0 (134.36) | 29.1; 26.6; 21.1 (138.4) | 14.6; 20.6; 24.4 (107.4) | 14.7; 15.3 (81) |
| 0.09 | NA | 20.7; 21.9; 22.2 (116.79) | 23.7; 21.4; 20.3 (117.8) | 20.4; 18.0 (103.8) | 11.0; 12.9 (65) |

SDS-PAGE and Western blot analysis of the recombinant cABCI revealed a partial fragmentation of the cABCI after prolonged storage at 4° C. The observation that degradation products are the same for both recombinant and native proteins suggests that the observed fragmentation may be due to an intrinsic property of cABCI.

The amino terminal end of the degradation products was sequenced. These results revealed that most of the degradation products were a mixture of protein fragments. Band #1: ATSNPAF (SEQ ID NO: 3); Band #2: ATSNPAF major (SEQ ID NO:4); NLNTSGD minor (SEQ ID NO:5); Band #3: ASNPAFD (SEQ ID NO:6) plus a mixture of sequences; Band #4: $X_1X_2NX_3V-X_4-X_5$ (SEQ ID NO:7) mixture wherein $X_1$ can be A or N; $X_2$ can be T or P; $X_3$ can be T or E; $X_4$ can be A or G; and $X_5$ can be F or E; Band #5: $X_1X_2NX_3X_5$ (SEQ ID NO:8) mixture wherein $X_1$ can be A or N; $X_2$ can be T or Y; $X_3$ can be T or P; $X_4$ can be A or E; $X_5$ can be A or G; Band #6: MQVNERD major (SEQ ID NO:9); GPRGAGT minor (SEQ ID NO:10); Band #7: no sequence was identified; Band #8: ATSNPAF (SEQ ID NO:11).

Example 12

This example shows the results of a purification method for the purification of chondroitinase AC.

The cells expressing chondroitinase AC were extracted using a square tip sonicator at a maximum speed of about 9. Sonication was performed for about 30 seconds. This was immediately followed by about 10 seconds with no sonication. These on/off steps were performed for a total of about 10 cycles. Each pellet was sonicated separately and then pooled. Extractions were rocked overnight at 4° C.

Following cell extraction of the chondroitinase AC the sonicated sample was analyzed on SDS-PAGE to analyze the solubility of the chondroitinase AC protein. The enzyme was detected primarily in the supernatant, implying that the protein is soluble. Purification was continued using a cation-exchange column to capture the enzyme.

All of the cell extract was loaded onto a 20 ml SP column. The extract was loaded onto the column at about 0.5 ml/min. The SP column was attached to the AKTA Explorer to view wash and elution peaks. The column was washed and the chondroitinase AC was eluted. The column fractions were then analyzed on SDS-PAGE to check purity and gel analysis revealed that the chondroitinase AC eluted from about 245 mM NaCl to about 370 mM NaCl. The SDS-PAGE analysis revealed that the eluted fractions contained relatively pure chondroitinase AC and they were pooled resulting in a total volume of 190 ml. The 190 ml of pooled fractions were concentrated using a 10,000 MWCO membrane (Millipore) down to a total volume of 105 ml with an absorbance (A280) of 1.47. The concentrated sample was then further purified using a gel filtration column.

Samples from the cation exchange step were loaded onto a S200 gel filtration column. Samples were eluted using 20 mM sodium acetate, 100 mM NaCl pH 5.5. The first purification run through the gel filtration column was analyzed on SDS-PAGE to check purity. The fractions that revealed a relatively pure chondroitinase AC were pooled. Following the fifth purification run through the column the fraction samples were once again checked on SDS-PAGE for purity. The fractions revealing a relatively pure chondroitinase AC from all seven runs were pooled for a total volume of 250 mls with an absorption (A280) of 0.431. The 250 mls were concentrated down to a total volume of 83 mls with absorption (A280) of 1.40.

Removal of endotoxin from the chondroitinase AC sample was achieved by further purification of the sample isolated from the gel filtration step. Samples were spun through a Q anion exchange membrane (as described elsewhere herein) and chondroitinase AC was collected in a flowthrough mode. This method was tested at about pH 5.5. 20 mM sodium acetate, pH 5.5, 100 mM NaCl was found to be an effective buffer for endotoxin binding to Q membranes, these pH and salt conditions are expected to remove approximately 75% endotoxin. The resulting absorption (A280) was 1.37. The final product was analyzed on SDS-PAGE for purity. The results revealed a pure chondroitinase AC with a molecular weight of about 50 to 75 kDa.

The purified chondroitinase AC was dialyzed into a volatile buffer of 0.1 M ammonium bicarbonate pH 8.0 overnight and aliquoted into small samples (about 1.0 ml), lyophilized and stored at 80° C. FIG. 12 shows the SDS-PAGE of the final purified chondroitinase AC.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A stable formulation comprising a chondroitinase and a sodium phosphate buffer at a concentration of about 750-1000 mM, wherein the chondroitinase retains at least 50% of activity at about 24 hours.

2. The formulation of claim 1, wherein said chondroitinase is purified.

3. The formulation of claim 1 wherein said chondroitinase is selected from the group consisting of chondroitinase ABCI, chondroitinase ABCII, chondroitinase AC, chondroitinase B mammalian enzymes with chondroitinase-like activity, Hyal1, Hyal2, Hyal3, Hyal4 and PH20.

4. The formulation of claim 1, wherein said chondroitinase is chondroitinase ABCI.

5. The formulation of claim 1, wherein said chondroitinase is chondroitinase AC.

6. The formulation of claim 1 further comprising sodium acetate.

7. The formulation of claim 1, wherein said formulation is at a pH of about 7.4.

8. The formulation of claim 3, wherein the chondroitinase ABC I is an amino acid sequence of SEQ ID NO: 2.

9. The formulation of claim 1, wherein the sodium phosphate buffer concentration is about 750 mM.

10. The formulation of claim 1, wherein the sodium phosphate buffer concentration is about 1000 mM.

11. The formulation of claim 1, wherein said chondroitinase is chondroitinase ABCII.

12. The formulation of claim 1, wherein said chondroitinase is chondroitinase B.

13. The formulation of claim 1, wherein said chondroitinase is chondroitinase Hyal1.

14. The formulation of claim 1, wherein said chondroitinase is chondroitinase Hyal2.

15. The formulation of claim 1, wherein said chondroitinase is chondroitinase Hyal3.

16. The formulation of claim 1, wherein said chondroitinase is chondroitinase Hyal4.

17. The formulation of claim 1, wherein said chondroitinase is chondroitinase PH20.

\* \* \* \* \*

SEQUENCE LISTING

<160> NUMBER OF SEQ ID NOS: 11

<210> SEQ ID NO 1
<211> LENGTH: 997
<212> TYPE: PRT
<213> ORGANISM: Proteus vulgaris

<400> SEQUENCE: 1

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285
```

```
Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720
```

-continued

```
Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
        740                 745                 750

Lys Asn Lys Asn Val Glu Thr Thr Leu Phe Gln His Ala Ile Thr Pro
    755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
        820                 825                 830

Phe Ser Ser Ala Trp Ile Asp His Ser Thr Arg Pro Lys Asp Ala Ser
    835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
            885                 890                 895

Gly Tyr Ala Phe Tyr Gln Pro Ala Ser Ile Glu Asp Lys Trp Ile Lys
        900                 905                 910

Lys Val Asn Lys Pro Ala Ile Val Met Thr His Arg Gln Lys Asp Thr
    915                 920                 925

Leu Ile Val Ser Ala Val Thr Pro Asp Leu Asn Met Thr Arg Gln Lys
930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
            965                 970                 975

Thr Glu Leu Thr Phe Thr Ser Tyr Phe Gly Ile Pro Gln Glu Ile Lys
        980                 985                 990

Leu Ser Pro Leu Pro
        995

<210> SEQ ID NO 2
<211> LENGTH: 841
<212> TYPE: PRT
<213> ORGANISM: Proteus vulgaris

<400> SEQUENCE: 2

Gln Asp Ser Ile Gly Arg Ser Leu Gly Ala Lys Val Asp Ser Ile Arg
1               5                   10                  15

Phe Lys Ala Pro Ser Asn Val Ser Gln Gly Glu Ile Tyr Ile Asp Arg
            20                  25                  30

Ile Met Phe Ser Val Asp Asp Ala Arg Tyr Gln Trp Ser Asp Tyr Gln
        35                  40                  45

Val Lys Thr Arg Leu Ser Glu Pro Glu Ile Gln Phe His Asn Val Lys
    50                  55                  60

Pro Gln Leu Pro Val Thr Pro Glu Asn Leu Ala Ala Ile Asp Leu Ile
65                  70                  75                  80

Arg Gln Arg Leu Ile Asn Glu Phe Val Gly Gly Glu Lys Glu Thr Asn
                85                  90                  95
```

```
Leu Ala Leu Glu Glu Asn Ile Ser Lys Leu Lys Ser Asp Phe Asp Ala
                100                 105                 110

Leu Asn Thr His Thr Leu Ala Asn Gly Gly Thr Gln Gly Arg His Leu
            115                 120                 125

Ile Thr Asp Lys Gln Ile Ile Tyr Gln Pro Glu Asn Leu Asn Ser
        130                 135                 140

Gln Asp Lys Gln Leu Phe Asp Asn Tyr Val Ile Leu Gly Asn Tyr Thr
145                 150                 155                 160

Thr Leu Met Phe Asn Ile Ser Arg Ala Tyr Val Leu Glu Lys Asp Pro
                165                 170                 175

Thr Gln Lys Ala Gln Leu Lys Gln Met Tyr Leu Leu Met Thr Lys His
            180                 185                 190

Leu Leu Asp Gln Gly Phe Val Lys Gly Ser Ala Leu Val Thr Thr His
        195                 200                 205

His Trp Gly Tyr Ser Ser Arg Trp Tyr Ile Ser Thr Leu Leu Met
    210                 215                 220

Ser Asp Ala Leu Lys Glu Ala Asn Leu Gln Thr Gln Val Tyr Asp Ser
225                 230                 235                 240

Leu Leu Trp Tyr Ser Arg Glu Phe Lys Ser Ser Phe Asp Met Lys Val
                245                 250                 255

Ser Ala Asp Ser Ser Asp Leu Asp Tyr Phe Asn Thr Leu Ser Arg Gln
            260                 265                 270

His Leu Ala Leu Leu Leu Glu Pro Asp Asp Gln Lys Arg Ile Asn
        275                 280                 285

Leu Val Asn Thr Phe Ser His Tyr Ile Thr Gly Ala Leu Thr Gln Val
            290                 295                 300

Pro Pro Gly Gly Lys Asp Gly Leu Arg Pro Asp Gly Thr Ala Trp Arg
305                 310                 315                 320

His Glu Gly Asn Tyr Pro Gly Tyr Ser Phe Pro Ala Phe Lys Asn Ala
                325                 330                 335

Ser Gln Leu Ile Tyr Leu Leu Arg Asp Thr Pro Phe Ser Val Gly Glu
            340                 345                 350

Ser Gly Trp Asn Ser Leu Lys Lys Ala Met Val Ser Ala Trp Ile Tyr
        355                 360                 365

Ser Asn Pro Glu Val Gly Leu Pro Leu Ala Gly Arg His Pro Leu Asn
370                 375                 380

Ser Pro Ser Leu Lys Ser Val Ala Gln Gly Tyr Tyr Trp Leu Ala Met
385                 390                 395                 400

Ser Ala Lys Ser Ser Pro Asp Lys Thr Leu Ala Ser Ile Tyr Leu Ala
                405                 410                 415

Ile Ser Asp Lys Thr Gln Asn Glu Ser Thr Ala Ile Phe Gly Glu Thr
            420                 425                 430

Ile Thr Pro Ala Ser Leu Pro Gln Gly Phe Tyr Ala Phe Asn Gly Gly
        435                 440                 445

Ala Phe Gly Ile His Arg Trp Gln Asp Lys Met Val Thr Leu Lys Ala
450                 455                 460

Tyr Asn Thr Asn Val Trp Ser Ser Glu Ile Tyr Asn Lys Asp Asn Arg
465                 470                 475                 480

Tyr Gly Arg Tyr Gln Ser His Gly Val Ala Gln Ile Val Ser Asn Gly
                485                 490                 495

Ser Gln Leu Ser Gln Gly Tyr Gln Gln Glu Gly Trp Asp Trp Asn Arg
            500                 505                 510

Met Pro Gly Ala Thr Thr Ile His Leu Pro Leu Lys Asp Leu Asp Ser
        515                 520                 525
```

```
Pro Lys Pro His Thr Leu Met Gln Arg Gly Glu Arg Gly Phe Ser Gly
    530                 535                 540

Thr Ser Ser Leu Glu Gly Gln Tyr Gly Met Met Ala Phe Asp Leu Ile
545                 550                 555                 560

Tyr Pro Ala Asn Leu Glu Arg Phe Asp Pro Asn Phe Thr Ala Lys Lys
                565                 570                 575

Ser Val Leu Ala Ala Asp Asn His Leu Ile Phe Ile Gly Ser Asn Ile
            580                 585                 590

Asn Ser Ser Asp Lys Asn Lys Asn Val Glu Thr Thr Leu Phe Gln His
        595                 600                 605

Ala Ile Thr Pro Thr Leu Asn Thr Leu Trp Ile Asn Gly Gln Lys Ile
    610                 615                 620

Glu Asn Met Pro Tyr Gln Thr Thr Leu Gln Gln Gly Asp Trp Leu Ile
625                 630                 635                 640

Asp Ser Asn Gly Asn Gly Tyr Leu Ile Thr Gln Ala Glu Lys Val Asn
                645                 650                 655

Val Ser Arg Gln His Gln Val Ser Ala Glu Asn Lys Asn Arg Gln Pro
            660                 665                 670

Thr Glu Gly Asn Phe Ser Ser Ala Trp Ile Asp His Ser Thr Arg Pro
        675                 680                 685

Lys Asp Ala Ser Tyr Glu Tyr Met Val Phe Leu Asp Ala Thr Pro Glu
    690                 695                 700

Lys Met Gly Glu Met Ala Gln Lys Phe Arg Glu Asn Asn Gly Leu Tyr
705                 710                 715                 720

Gln Val Leu Arg Lys Asp Lys Asp Val His Ile Ile Leu Asp Lys Leu
                725                 730                 735

Ser Asn Val Thr Gly Tyr Ala Phe Tyr Gln Pro Ala Ser Ile Glu Asp
            740                 745                 750

Lys Trp Ile Lys Lys Val Asn Lys Pro Ala Ile Val Met Thr His Arg
        755                 760                 765

Gln Lys Asp Thr Leu Ile Val Ser Ala Val Thr Pro Asp Leu Asn Met
    770                 775                 780

Thr Arg Gln Lys Ala Ala Thr Pro Val Thr Ile Asn Val Thr Ile Asn
785                 790                 795                 800

Gly Lys Trp Gln Ser Ala Asp Lys Asn Ser Glu Val Lys Tyr Gln Val
                805                 810                 815

Ser Gly Asp Asn Thr Glu Leu Thr Phe Thr Ser Tyr Phe Gly Ile Pro
            820                 825                 830

Gln Glu Ile Lys Leu Ser Pro Leu Pro
        835                 840

<210> SEQ ID NO 3
<211> LENGTH: 7
<212> TYPE: PRT
<213> ORGANISM: Artificial
<220> FEATURE:
<223> OTHER INFORMATION: protein fragment

<400> SEQUENCE: 3

Ala Thr Ser Asn Pro Ala Phe
1               5

<210> SEQ ID NO 4
<211> LENGTH: 7
<212> TYPE: PRT
<213> ORGANISM: Artificial
<220> FEATURE:
<223> OTHER INFORMATION: protein fragment
```

```
<400> SEQUENCE: 4

Ala Thr Ser Asn Pro Ala Phe
1               5

<210> SEQ ID NO 5
<211> LENGTH: 7
<212> TYPE: PRT
<213> ORGANISM: Artificial
<220> FEATURE:
<223> OTHER INFORMATION: protein fragment

<400> SEQUENCE: 5

Asn Leu Asn Thr Ser Gly Asp
1               5

<210> SEQ ID NO 6
<211> LENGTH: 7
<212> TYPE: PRT
<213> ORGANISM: Artificial
<220> FEATURE:
<223> OTHER INFORMATION: protein fragment

<400> SEQUENCE: 6

Ala Ser Asn Pro Ala Phe Asp
1               5

<210> SEQ ID NO 7
<211> LENGTH: 7
<212> TYPE: PRT
<213> ORGANISM: Artificial
<220> FEATURE:
<223> OTHER INFORMATION: protein fragment
<220> FEATURE:
<221> NAME/KEY: misc_feature
<222> LOCATION: (1)..(1)
<223> OTHER INFORMATION: Xaa can be A or N
<220> FEATURE:
<221> NAME/KEY: misc_feature
<222> LOCATION: (2)..(2)
<223> OTHER INFORMATION: Xaa can be T or P
<220> FEATURE:
<221> NAME/KEY: misc_feature
<222> LOCATION: (4)..(4)
<223> OTHER INFORMATION: Xaa can be T or E
<220> FEATURE:
<221> NAME/KEY: misc_feature
<222> LOCATION: (6)..(6)
<223> OTHER INFORMATION: Xaa can be A or G
<220> FEATURE:
<221> NAME/KEY: misc_feature
<222> LOCATION: (7)..(7)
<223> OTHER INFORMATION: Xaa can be F or E

<400> SEQUENCE: 7

Xaa Xaa Asn Xaa Val Xaa Xaa
1               5

<210> SEQ ID NO 8
<211> LENGTH: 6
<212> TYPE: PRT
<213> ORGANISM: Artificial
<220> FEATURE:
<223> OTHER INFORMATION: protein fragment
<220> FEATURE:
<221> NAME/KEY: misc_feature
<222> LOCATION: (1)..(1)
<223> OTHER INFORMATION: Xaa can be A or N
<220> FEATURE:
<221> NAME/KEY: misc_feature
<222> LOCATION: (2)..(2)
<223> OTHER INFORMATION: Xaa can be T or Y
```

```
<220> FEATURE:
<221> NAME/KEY: misc_feature
<222> LOCATION: (4)..(4)
<223> OTHER INFORMATION: Xaa can be T or P
<220> FEATURE:
<221> NAME/KEY: misc_feature
<222> LOCATION: (5)..(5)
<223> OTHER INFORMATION: Xaa can be A or E
<220> FEATURE:
<221> NAME/KEY: misc_feature
<222> LOCATION: (6)..(6)
<223> OTHER INFORMATION: Xaa can be A or G

<400> SEQUENCE: 8

Xaa Xaa Asn Xaa Xaa Xaa
1               5

<210> SEQ ID NO 9
<211> LENGTH: 7
<212> TYPE: PRT
<213> ORGANISM: Artificial
<220> FEATURE:
<223> OTHER INFORMATION: protein fragment

<400> SEQUENCE: 9

Met Gln Val Asn Glu Arg Asp
1               5

<210> SEQ ID NO 10
<211> LENGTH: 7
<212> TYPE: PRT
<213> ORGANISM: Artificial
<220> FEATURE:
<223> OTHER INFORMATION: protein fragment

<400> SEQUENCE: 10

Gly Pro Arg Gly Ala Gly Thr
1               5

<210> SEQ ID NO 11
<211> LENGTH: 7
<212> TYPE: PRT
<213> ORGANISM: Artificial
<220> FEATURE:
<223> OTHER INFORMATION: protein fragment

<400> SEQUENCE: 11

Ala Thr Ser Asn Pro Ala Phe
1               5
```